(12) United States Patent
Starkebaum et al.

(10) Patent No.: US 7,957,807 B2
(45) Date of Patent: Jun. 7, 2011

(54) GASTRIC ELECTRICAL STIMULATION WITH THERAPY WINDOW ANTI-DESENSITIZATION FEATURE

(75) Inventors: Warren L. Starkebaum, Plymouth, MN (US); Charlene X. Yuan, Woodbury, MN (US); Roland C. Maude-Griffin, Edina, MN (US); Luiz Geraldo Pivotto, Geneva (CH)

(73) Assignee: Medtronic, Inc., Minneapolis, MN (US)

( * ) Notice: Subject to any disclaimer, the term of this patent is extended or adjusted under 35 U.S.C. 154(b) by 183 days.

(21) Appl. No.: 12/236,852

(22) Filed: Sep. 24, 2008

(65) Prior Publication Data

US 2009/0088818 A1   Apr. 2, 2009

Related U.S. Application Data

(60) Provisional application No. 60/997,058, filed on Oct. 1, 2007.

(51) Int. Cl.
*A61N 1/18* (2006.01)
(52) U.S. Cl. .......................................... 607/40; 607/133
(58) Field of Classification Search .................. 607/40, 607/133
See application file for complete search history.

(56) References Cited

U.S. PATENT DOCUMENTS

| | | | |
|---|---|---|---|
| 5,188,104 A | 2/1993 | Wernicke et al. |
| 5,231,988 A | 8/1993 | Wernicke et al. |
| 5,292,344 A | 3/1994 | Douglas |
| 5,540,730 A | 7/1996 | Terry, Jr. et al. |
| 5,690,691 A | 11/1997 | Chen et al. |
| 6,026,326 A | 2/2000 | Bardy |
| 6,115,635 A | 9/2000 | Bourgeois |
| 6,449,511 B1 | 9/2002 | Mintchev et al. |
| 6,591,137 B1 | 7/2003 | Fischell et al. |
| 7,050,856 B2 | 5/2006 | Stypulkowski |
| 7,177,693 B2 | 2/2007 | Starkebaum |
| 7,343,201 B2 | 3/2008 | Mintchev |
| 2002/0161414 A1 | 10/2002 | Flesler et al. |
| 2002/0198470 A1 | 12/2002 | Imran et al. |
| 2004/0059393 A1 | 3/2004 | Policker et al. |
| 2004/0147976 A1 | 7/2004 | Gordon et al. |
| 2004/0230255 A1 | 11/2004 | Dobak, III |

(Continued)

FOREIGN PATENT DOCUMENTS

| | | |
|---|---|---|
| WO | WO/91/06340 | 5/1991 |
| WO | WO 02/28477 A1 | 4/2002 |
| WO | WO2007/018786 A2 | 2/2007 |

OTHER PUBLICATIONS

Cees de Graaf et al., "Biomarkers of satiation and satiety," Am. J. Clin. Nut., 2004, vol. 79, pp. 946-961, 2004.

(Continued)

*Primary Examiner* — Carl H Layno
*Assistant Examiner* — Brian T Gedeon
(74) *Attorney, Agent, or Firm* — Shumaker & Sieffert, P.A.

(57) ABSTRACT

The disclosure is directed to gastric stimulation programmers, stimulators and methods for controlling delivery of gastric stimulation therapy to maintain the efficacy of the therapy over time. Maintaining the efficacy of gastric stimulation therapy may be possible by implementing one or more anti-desensitization features in a gastric stimulation controller or stimulator. As electrical stimulation therapy is continuously delivered to a patient, the stimulated tissue may become desensitized to the electrical stimulation therapy such that the beneficial effect of the electrical stimulation is diminished. Once desensitization occurs, the affected tissue may not respond favorably to electrical stimulation therapy. Application of one or more anti-desensitization features to control gastric stimulation therapy may reduce or prevent desensitization and effectively extend the efficacy of the therapy over time.

26 Claims, 18 Drawing Sheets

U.S. PATENT DOCUMENTS

| | | | |
|---|---|---|---|
| 2005/0065575 | A1 | 3/2005 | Dobak |
| 2005/0131493 | A1 | 6/2005 | Boveja et al. |
| 2005/0137643 | A1 | 6/2005 | Mintchev |
| 2005/0149141 | A1 | 7/2005 | Starkebaum |
| 2005/0149142 | A1 | 7/2005 | Starkebaum |
| 2005/0222638 | A1 | 10/2005 | Foley et al. |
| 2006/0095088 | A1 | 5/2006 | DeRidder |
| 2006/0173507 | A1 | 8/2006 | Mrva et al. |
| 2006/0247717 | A1 | 11/2006 | Starkebaum |
| 2006/0247718 | A1 | 11/2006 | Starkebaum |
| 2007/0282387 | A1 | 12/2007 | Starkebaum |

OTHER PUBLICATIONS

U.S. Patent Application entitled "Gastric Electrical Stimulation With Lockout Interval Anti-Desensitization Feature", U.S. Appl. No. 12/236,836, filed Sep. 24, 2008, Starkebaum et al.

U.S. Patent Application entitled "Gastric Electrical Stimulation With Multi-Site Stimulation Anti-Desensitization Feature", U.S. Appl. No. 12/236,924, filed Sep. 24, 2008, Starkebaum et al.

Notification of Transmittal of the International Search Report and the Written Opinion of the International Searching Authority for corresponding patent application No. PCT/US2008/011038, mailed Jan. 14, 2008, 17 pages.

Valerio Cigaina, MD., "Gastric Pacing as Therapy for Morbid Obesity: Preliminary Results," Obesity Surgery, vol. 12, No. Suppl. 1, Apr. 1, 2002, 5 pages.

Lee et al., "Occupational asthma due to maleic anhydride," Obesity Surgery, vol. 15, No. 4, Apr. 2005, 3 pages.

Lei et al., "Effects and Mechanisms of Implantable Gastric Stimulation on Gastric Distention in Conscious Dogs," Obesity Surgery, vol. 15, 2005, pp. 528-533.

Reply to Written Opinion for corresponding patent application No. PCT/US2008/011038, filed Jun. 4, 2009, 4 pages.

Notification of Transmittal of the International Preliminary Report on Patentability for corresponding patent application No. PCT/US2008/011038, mailed Sep. 7, 2009, 8 pages.

Office Action for U.S. Appl. No. 12/236,924, mailed May 28, 2010, 10 pages.

Response to Office Action for U.S. Appl. No. 12/236,924, filed Aug. 27, 2010, 16 pages.

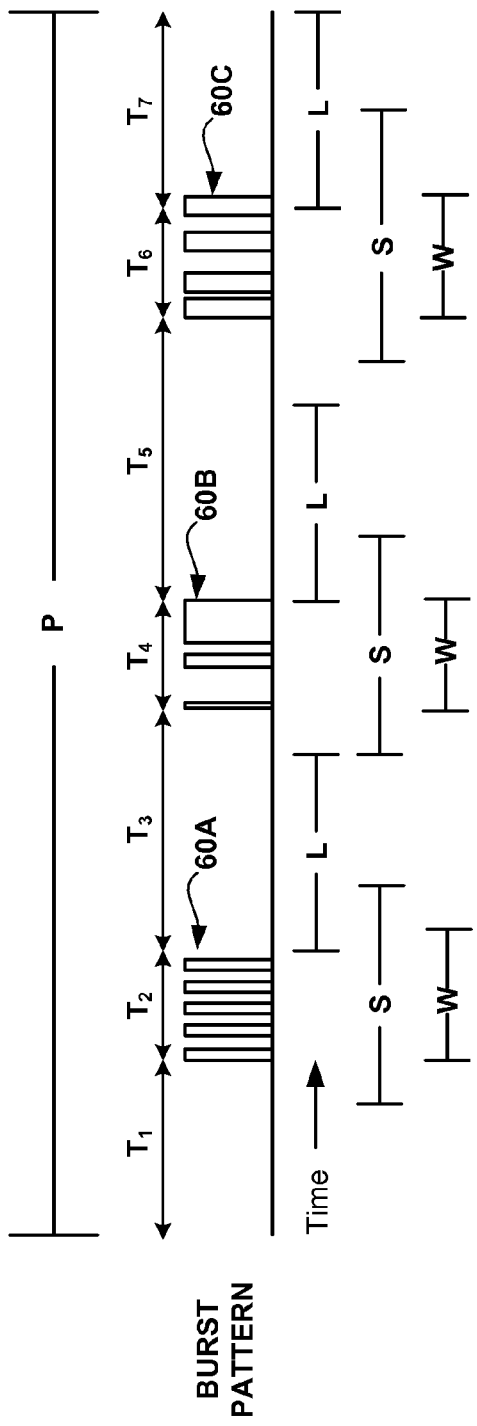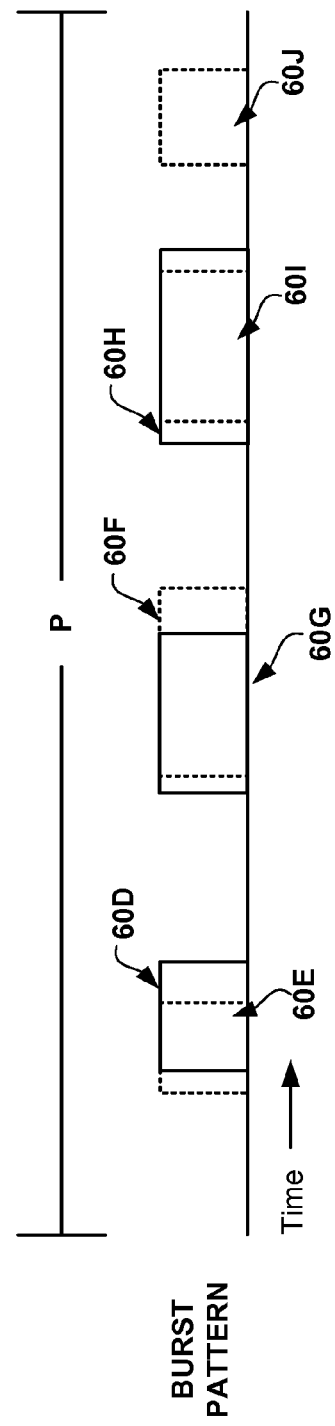
FIG. 5D
FIG. 5E

GASTRIC ELECTRICAL STIMULATION WITH THERAPY WINDOW ANTI-DESENSITIZATION FEATURE

This application claims the benefit of U.S. provisional application No. 60/997,058, filed Oct. 1, 2007, the entire content of which is incorporated herein by reference.

TECHNICAL FIELD

The disclosure relates to implantable medical devices and, more particularly, implantable medical devices for gastric electrical stimulation.

BACKGROUND

Obesity is a serious health problem for many people. Patients who are overweight often have problems with mobility, sleep, high blood pressure, and high cholesterol. Some other serious risks also include diabetes, cardiac arrest, stroke, kidney failure, and mortality. In addition, an obese patient may experience psychological problems associated with health concerns, social anxiety, and generally poor quality of life.

Certain diseases or conditions can contribute to additional weight gain in the form of fat, or adipose tissue. However, healthy people may also become overweight as a net result of excess energy consumption and insufficient energy expenditure. Reversal of obesity is possible but difficult. Once the patient expends more energy than is consumed, the body will begin to use the energy stored in the adipose tissue. This process will slowly remove the excess fat from the patient and lead to better health. Some patients require intervention to help them overcome their obesity. In these severe cases, nutritional supplements, prescription drugs, or intense diet and exercise programs may not be effective.

Surgical intervention is a last resort treatment for some obese patients who are considered morbidly obese. One common surgical technique is the Roux-en-Y gastric bypass surgery. In this technique, the surgeon staples or sutures off a large section of the stomach to leave a small pouch that holds food. Next, the surgeon severs the small intestine at approximately mid length and attaches the distal section of the small intestine to the pouch portion of the stomach. This procedure limits the amount of food the patient can ingest to a few ounces and limits the amount of time that ingested food may be absorbed through the shorter length of the small intestine. While this surgical technique may be very effective, it poses significant risks of unwanted side effects, including malnutrition, and death.

Electrical stimulation therapy is an alternative to surgical intervention and may be effective in treating obesity either alone or in combination with diet and exercise. For electrical stimulation therapy, a patient is fitted with an implanted electrical stimulator that delivers electrical stimulation pulses to the patient's stomach via electrodes carried by one or more leads. The electrical stimulation therapy may be configured to induce a sensation of fullness or nausea in the patient, thereby discouraging excessive food intake. In addition, in some cases, the electrical stimulation therapy may be configured to increase or decrease gastric motility, reduce appetite or increase satiety, or induce a sensation of abdominal discomfort on ingestion of a meal, so that caloric absorption is reduced. Hence, electrical stimulation therapy may be effective in causing weight loss by discouraging food intake and/or reducing caloric absorption.

SUMMARY

The disclosure is directed to various techniques for controlling delivery of gastric electrical stimulation therapy to maintain the efficacy of the therapy over time. Maintaining the efficacy of gastric electrical stimulation therapy may be possible by implementing one or more anti-desensitization features in a gastric electrical stimulation programmer or gastric electrical stimulator. The anti-desensitization features may limit application of delivery of electrical stimulation to selected times, durations, frequencies, electrode combinations, and/or tissue sites. The anti-desensitization features may be implemented independently or in combination with one another to reduce or delay desensitization of gastric tissue, and thereby promote effective and/or prolonged therapy.

In one aspect, the disclosure provides a method comprising receiving a request to deliver gastric electrical stimulation therapy to a patient, prohibiting delivery of the gastric electrical stimulation therapy if the request is received within a lockout period following a previous delivery of the gastric electrical stimulation therapy, and permitting delivery of the gastric electrical stimulation therapy if the request is not received within a lockout period following the previous delivery of gastric stimulation therapy.

In another aspect, the disclosure provides a system comprising a stimulator that delivers gastric electrical stimulation therapy to a patient, and an external programmer that controls the stimulator to deliver the gastric electrical stimulation therapy, wherein one of the external programmer or the stimulator receives a request to deliver the electrical gastric stimulation therapy to the patient, prohibits delivery of the gastric stimulation therapy by the stimulator if the request is received within a lockout period following a previous delivery of gastric stimulation therapy, and permits delivery of the gastric stimulation therapy by the stimulator if the request is not received within a lockout period following the previous delivery of gastric stimulation therapy.

In an additional aspect, the disclosure provides an external programmer for a gastric electrical stimulator, the programmer comprising a user interface that receives a request to deliver the gastric electrical stimulation therapy to a patient, and a processor that controls the gastric electrical stimulator to prohibit delivery of the gastric electrical stimulation therapy by the stimulator if the request is received within a lockout period following a previous delivery of gastric electrical stimulation therapy, and permit delivery of the gastric electrical stimulation therapy by the stimulator if the request is not received within a lockout period following the previous delivery of gastric stimulation therapy.

In another aspect, the disclosure provides a gastric electrical stimulator comprising a stimulation generator that delivers gastric electrical stimulation therapy, an interface that receives a request to deliver the electrical gastric stimulation therapy to a patient, and a processor that controls the stimulation generator such that the stimulator generator prohibits delivery of the gastric stimulation therapy by the stimulator if the request is received within a lockout period following a previous delivery of gastric stimulation therapy, and permits delivery of the gastric stimulation therapy by the stimulator if the request is not received within a lockout period following the previous delivery of gastric stimulation therapy.

In another aspect, the disclosure provides a method comprising delivering gastric electrical stimulation therapy from an implantable gastric electrical stimulator to a patient for a first period of time, and denying a patient request received by an external programmer to deliver the gastric electrical stimulation therapy from the implantable gastric electrical stimulator to the patient for a lockout period of time following the first period of time.

In a further aspect, the disclosure provides a method comprising delivering electrical stimulation therapy to a gastrointestinal organ of a patient for a first period of time, wherein the first period of time is selected to produce a desired therapeutic effect for a second period of time that extends at least in part beyond an end of the first period of time.

In another aspect, the disclosure provides a gastric electrical stimulation device comprising an electrical stimulation generator generates electrical stimulation therapy for a first period of time, and one or more implantable electrodes coupled to deliver the electrical stimulation therapy to a gastrointestinal organ of a patient, wherein the first period of time is selected to produce a desired therapeutic effect for a second period of time that extends at least in part beyond an end of the first period of time.

In another aspect, the disclosure provides an external programmer device for a gastric electrical stimulator, the programmer comprising a processor that controls the electrical stimulation generator to generate electrical stimulation therapy for a first period of time for delivery to a gastrointestinal organ of a patient, wherein the first period of time is selected to produce a desired therapeutic effect for a second period of time that extends at least in part beyond an end of the first period of time.

In another aspect, the disclosure provides a method for gastric stimulation with reduced desensitization, the method comprising delivering first electrical stimulation therapy to a gastrointestinal organ of a patient via a first electrode combination positioned at a first position on the gastrointestinal organ for a first period of time greater than or equal to approximately 30 seconds, and delivering second electrical stimulation therapy to the gastrointestinal organ via a second electrode combination positioned at a second position on the gastrointestinal organ for a second period of time greater than or equal to approximately 30 seconds, wherein the first and second electrical stimulation therapies are configured to produce a substantially identical therapeutic result.

In an additional aspect, the disclosure provides a gastrointestinal electrical stimulation device comprising a first electrode combination implantable at a first position on a gastrointestinal organ of a patient, a second electrode combination implantable at a second position on the gastrointestinal organ, and a stimulation generator that delivers first electrical stimulation therapy to the gastrointestinal organ via the first electrode combination for a first period of time greater than or equal to approximately 30 seconds, and delivers second electrical stimulation therapy to the gastrointestinal organ via a second electrode combination for a second period of time greater than or equal to approximately 30 seconds, wherein the first and second electrical stimulation therapies are configured to produce a substantially identical therapeutic result.

The details of one or more embodiments of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 5A-5E are example timing diagrams illustrating different modes for delivering electrical stimulation pulses.

DETAILED DESCRIPTION

Figure 1:
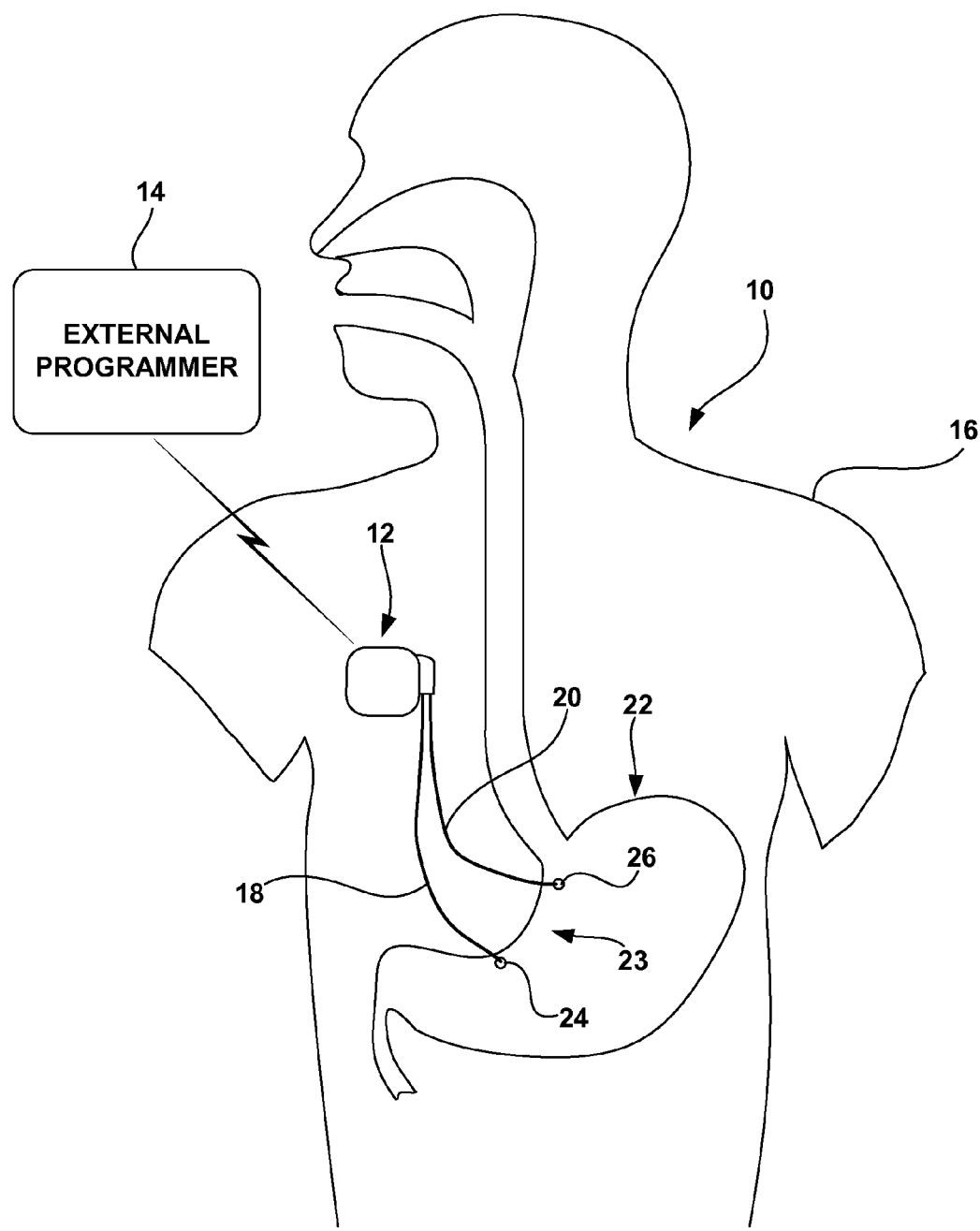
FIG. 1 is a schematic diagram illustrating an example implantable gastric electrical stimulation system.

The disclosure is directed to techniques for controlling delivery of gastric stimulation therapy to maintain the efficacy of the therapy over time. Maintaining the efficacy of gastric stimulation therapy may be possible by implementing one or more anti-desensitization features in an external gastric stimulation programmer and/or gastric electrical stimulator to limit application of electrical stimulation to selected frequency, times, tissue sites, and/or durations. The anti-desensitization features may be implemented independently or in combination with one another to reduce or delay desensitization of gastric tissue, and thereby promote effective and/or prolonged therapy.

The gastric stimulator may be external or implantable. An external stimulator may deliver stimulation via one or more percutaneously implantable leads. An implantable stimulator may deliver stimulation via one or more fully implantable leads. An external programmer such as a patient programmer or physician programmer may communicate with a gastric electrical stimulator, e.g., by radio frequency (RF) wireless telemetry or other techniques. Gastric electrical stimulation generally refers to electrical stimulation of the stomach, small intestine or other organs within the gastrointestinal tract, and may alternatively be referred to as gastrointestinal electrical stimulation.

Desensitization may generally refer to a state of accommodation in which delivery of electrical stimulation to a particular tissue site is less effective in achieving a desired therapeutic result. Incorporation of anti-desensitization features in a programmer and/or stimulator may allow gastric stimulation therapy to be more effective in treating the patient for a longer period of time when compared to standard therapy. This extended period of effective therapy may reduce the chance that the patient will need to pursue different treatment options due to electrical stimulation desensitization. In addition, in some cases, one or more anti-desensitization features may reduce the amount and duration of stimulation provided to the patient, which may conserve battery power and extend the operational life of an implantable stimulator.

As electrical stimulation therapy is continuously delivered to a patient, the stimulated tissue may become desensitized to the electrical stimulation therapy such that the beneficial effect of the electrical stimulation is diminished. Once desensitization occurs, the affected tissue may no longer respond favorably to electrical stimulation therapy. Application of one or more anti-desensitization features to control gastric stimulation therapy, either via an external gastric stimulation programmer or an implantable gastric stimulator, or both, may reduce or prevent desensitization and effectively extend the efficacy of the therapy over time.

In accordance with this disclosure, an external gastric stimulation programmer or gastric electrical stimulator may utilize one or more anti-desensitization features that extend the efficacy of gastric stimulation therapy delivered to the patient by the gastric stimulator. The external gastric stimulation programmer may be, in some cases, a patient programmer that communicates within the gastric stimulator, e.g., by wireless telemetry. The anti-desensitization features may include at least one of a lockout period feature, a therapy window feature, a multi-site stimulation feature, a therapy schedule feature, a burst pattern variation feature, and a burst pattern parameter selection feature.

After therapy has been delivered for a permitted period of time, either by way of a therapy window feature or otherwise, a lockout period feature may be applied by the programmer or stimulator to prevent the patient from reinitiating further stimulation therapy until the lockout period expires, thus preventing excessively frequent stimulation. If a patient attempts to reactivate stimulation before the lockout period has expired, the programmer or stimulator may prohibit delivery of stimulation. In addition, the programmer may notify the patient that stimulation cannot be activated until the lockout period has expired.

The length of the lockout period may be selected to ensure that subject tissue has a sufficient period of time to recover between successive applications of electrical stimulation in order to avoid or delay desensitization. The lockout period may be, for example, on the order of several seconds, minutes or hours. The lockout period feature may interrupt stimulation for certain periods of time, which may allow time for neurotransmitters to be replenished at the cell level.

Upon receipt of a request to delivery stimulation therapy, a programmer or stimulator may apply the lockout period feature to prohibit delivery of the gastric electrical stimulation therapy if the request is received within a lockout period following a previous delivery of the gastric electrical stimulation therapy, and deliver the gastric electrical stimulation therapy if the request is not received within a lockout period following the previous delivery of gastric stimulation therapy.

Using a therapy window feature, the programmer or stimulator may permit delivery of therapy for only a relatively short duration such that the patient may rely upon residual stimulation effects to prolong a desired therapeutic effect after stimulation has been stopped. In this manner, the therapy window prevents stimulation for an excessive period of time. In some cases, the therapy window W may represent approximately a minimum duration of the gastric stimulation therapy that has been determined or estimated to be effective in producing desired therapeutic effects for a desired period of time, including a period of time after termination of the gastric stimulation therapy. In some cases, the therapy window W may represent approximately the minimum duration plus a time margin to ensure the desired therapeutic effect for the desired period of time.

At the same time, although it may be determined as a function of the minimum duration sufficient to produce a therapeutic effect for a desired period of time, the therapy window W also may specify the maximum period for which stimulation may be delivered at a given time. If the minimum duration defining the therapy window W is sufficient to achieve a desired therapeutic effect for a given period of time, then delivery of stimulation beyond this duration may be considered inefficient. Accordingly, the therapy window W may specify the maximum duration of stimulation to be delivered, and at the same time be determined according to the minimum duration sufficient to achieve a desired therapeutic effect for a specified period of time.

If the minimum period of time sufficient to maintain a desired therapeutic effect for a desired period of time x, given a set of stimulation parameters, is y minutes, then the therapy window W may be approximately y minutes in length, possibly plus or minus a margin of time. Hence, when the stimulator delivers stimulation during the therapy window W, it may deliver stimulation for a maximum of y minutes. However, the therapeutic effect may be produced for x minutes. Application of stimulation for the length of the therapy window W, with appropriate stimulation parameters, may be sufficient to cause a desired therapeutic effect that remains at least partially intact for a prolonged period of time even after delivery of stimulation is terminated. In this case, a desired therapeutic effect can be achieved for an extended period of time beyond the actual time that electrical stimulation is applied to the patient.

To implement the therapy window feature, a programmer or stimulator may deliver electrical stimulation therapy to a gastrointestinal organ of a patient for a first period of time, wherein the first period of time is selected to produce a desired therapeutic effect for a second period of time that extends at least in part beyond an end of the first period of time. In this case, the first period of time corresponds to the therapy window W, and the second period of time corresponds to the period of time for which the desired therapeutic effect persists. The second period of time, in some cases, may be greater than the first period of time. The first period of time may be selected, in some cases, as approximately a minimum period of time sufficient to produce the desired therapeutic effect for the second period of time. As an example, the desired therapeutic effect may be a change in gastric muscle tone indicated by a degree of gastric distention. The degree of gastric distention may correspond to a percentage increase in gastric volume.

The programmer or stimulator may apply a therapy schedule feature to permit delivery of stimulation therapy only during predetermined therapy schedule times S, e.g., coincident with ordinary meal or snack times for obesity therapy or motility regulation. The therapy schedule may be customized for particular patients to match different meal times, snack times and lifestyles. Therapy windows W may be applied at different times within a permitted schedule time S. Notably, the schedule time S is different from the first and second periods referred to above with respect to the therapy window feature, as well as the lockout period described above. In contrast, the schedule times specify times on a schedule at which stimulation may be delivered, possibly subject to other anti-desensitization features such as the lockout period and therapy window features.

When delivery of stimulation therapy is requested at a time that does not fall within one of the predetermined therapy schedule time S on the therapy schedule, the programmer or stimulator may prohibit delivery of stimulation therapy. In addition, the programmer may notify the patient that stimulation cannot be activated until the next permitted time S on the therapy schedule. Hence, stimulation may be off between therapy time S on the therapy schedule, helping to prevent or delay desensitization of stimulated tissue. Delivery of stimulation therapy may be requested by a patient or requested internally within a programmer or stimulator as an automated request, e.g., according to a therapy schedule.

Using a multi-site stimulation feature, the programmer or stimulator may select different combinations of electrodes to deliver stimulation to different tissue sites at different times. The different times may partially overlap or not overlap. The multi-site stimulation feature may be applied such that different electrode combinations are used within a therapy window W, or within different therapy windows, or within different periods of time on the therapy schedule, or when stimulation is otherwise applied. In this manner, the programmer or stimulator may distribute electrical stimulation over a larger number of varied tissue sites over time to prevent rapid desensitization that could otherwise occur if stimulation was delivered to a single tissue site. In some cases, the selection of different electrode combinations for stimulation at different times may be ordered, randomized, or pseudo-randomized such that stimulation is delivered to different tissue sites over time in order to prevent or delay desensitization of a particular tissue site.

As an example, to implement an multi-site stimulation feature, a programmer or stimulator may control delivery of gastric stimulation by delivering first electrical stimulation therapy to a gastrointestinal organ via a first electrode combination associated with a first position on the gastrointestinal organ for a first period of time, and delivering second electrical stimulation therapy to the gastrointestinal organ via a second electrode combination associated with a second position on the gastrointestinal organ for a second period of time. The periods of time used for the multi-site stimulation feature, like the periods used for the lockout period and therapy window, are different from the therapy schedule periods P.

The electrode combinations used for the multi-site stimulation feature, may be associated with the positions on the gastrointestinal organ in the sense that electrodes in the combinations are generally co-located with the positions, or otherwise positioned to direct stimulation to the positions as different stimulated tissue sites. In some cases, however, each electrode combination may include at least one electrode in common with one another, e.g., such as a common ground electrode on a device housing in a unipolar arrangement or elsewhere in a bipolar or multipolar arrangement. In addition, at least some of the electrodes forming an electrode combination may be carried by the same lead or different leads.

In some examples, each of the first and second periods of time may be greater than or equal to approximately 30 seconds. In this manner, stimulation may be applied to a tissue site for a period of time sufficient to support a desired therapeutic effect, but then be shifted to another tissue site to mitigate tissue desensitization. In other cases, each of the first and second periods of time may be greater than or equal to approximately one minute, five minutes, one hour, or one day. The first and second periods may reside within different therapy windows W or different schedule periods P, or within the same therapy windows W or schedule periods P.

The first and second electrical stimulation therapies delivered to different tissue sites are configured to produce a substantially identical therapeutic result, such as promotion of gastric distention, nausea or discomfort to discourage food intake by a patient. In other words, each electrode combination delivers stimulation with parameters selected to produce substantially the same result, such as gastric distention. In some cases, the first and second electrical stimulation therapies may be configured to reduce, increase, or maintain gastric motility. In other cases, the first and second stimulation therapies are configured to not reduce, increase, or maintain gastric motility, and instead to promote gastric distention, nausea or discomfort, as mentioned above.

Using the multi-site feature, the programmer or stimulator may control delivery of stimulation via two or more different electrode combinations, e.g., on an interleaved basis during a given therapy window W or during different therapy windows. In this manner, the stimulation therapy is distributed among different tissue sites as it is delivered to prevent rapid desensitization at a single tissue site. For example, stimulation may be delivered to a first electrode combination associated with a first tissue site and then delivered to a second electrode combination associated with a second tissue site, e.g., as interleaved, alternating pulse trains, bursts, or the like, within a given therapy window or therapy period. As mentioned above, the stimulation parameters, electrode combinations and associated tissue sites may be selected to support a substantially similar therapeutic effect, yet reduce the amount of time each of the tissue sites receives stimulation, thereby preventing of delaying desensitization.

The programmer or stimulator may apply a burst pattern variation feature as a further anti-desensitization feature to vary the timing and/or duration of burst patterns of stimulation delivered to a patient. A pulse burst generally refers to a group of stimulation pulses, e.g., by gating a continuous pulse train on and off. During the ON period, a pulse burst is produced. A burst pattern, as used herein, generally refers to a set of multiple pulse bursts. To reduce or delay desensitization, burst patterns can be produced by gating bursts ON and OFF. During the ON period, the stimulator delivers bursts of pulses. During the OFF period, no pulses or bursts are delivered. The pulse bursts can be gated ON and OFF repeatedly throughout the day to deliver burst patterns at selected times. The timing and/or duration of the burst patterns may be fixed during the day or varied. In either case, delivery of selected burst patterns instead of continuous bursts or continuous pulse trains may be effective in treating as well as in preventing or delaying desensitization.

With the burst pattern parameter selection feature, the programmer or stimulator may vary one or more stimulation parameter values over a series of burst patterns, as described above. For example, instead of delivering stimulation in continuous pulses, or bursts of pulses, the programmer or stimulator may control stimulation such that it is delivered in burst patterns, wherein each burst pattern includes multiple pulse bursts and each burst pattern is separated in time from another burst pattern. The programmer or stimulator may vary stimulation parameters such as amplitude, pulse width, and pulse rate of pulses among different burst patterns as another anti-desensitization feature, e.g., to prevent or delay desensitization of stimulated tissue.

The anti-desensitization features described above may be applied by a programmer, a stimulator or both to limit or prevent desensitization. In addition, the anti-desensitization features may be used individually or in combinations of two, three or more additional anti-desensitization features to extend or maintain efficacious therapy by preventing rapid desensitization. In some cases, some or all of the anti-desensitization features may be applied by the programmer, stimulator, or both. Also, in some embodiments, one or more anti-desensitization features may be applied by the programmer while one or more other anti-desensitization features may be applied by the stimulator. The anti-desensitization features may be applied by a programmer in selectively controlling a stimulator via commands or requests transmitted to the stimulator, and may be applied by a stimulator by controlling stimulation generated by the stimulator.

In general, the disclosure is directed to methods for controlling delivery of gastric electrical stimulation therapy to maintain the efficacy of the therapy over time. Gastric electrical stimulation therapy may be delivered to the gastrointestinal tract, e.g., the stomach and/or small intestine, to treat a disease or disorder such as obesity or gastroparesis. In the case of obesity therapy, for example, electrical stimulation of the stomach may be configured to cause the stomach to undergo a change in gastric muscle tone, which may be indicated by distention, and induce a feeling of satiety within the patient. As a result, the patient may reduce caloric intake because the patient has a reduced urge to eat. Alternatively, or additionally, electrical stimulation of the stomach may be configured to induce nausea in the patient and thereby discourage eating. In addition, electrical stimulation of the duodenum may be configured to increase motility in the small intestine, thereby reducing caloric absorption. For gastroparesis, gastric stimulation of the stomach and/or duodenum may be configured to increase or regulate motility. In each case, however, consistent electrical stimulation of the same tissue over time may desensitize the tissue to the electrical stimulation, resulting in accommodation and reduced therapeutic efficacy.

Patients receiving implantable gastric stimulators may report an initial sensation that subsides over time. One explanation is that one or more neurotransmitters necessary for depolarization of a nerve or muscle cell may become depleted over time when a nerve or muscle cell is stimulated continuously over time. There may be insufficient time for this neurotransmitter to be replenished to a level sufficient for the nerve or muscle cell to fire in response to electrical stimulation. This resulting desensitization may cause diminished efficacy of the electrical stimulation therapy to a point where the therapy is no longer beneficial in treating the patient. For this reason, it may be beneficial to implement one or more anti-desensitization features in the control of the delivery of the therapy, either in a programmer or stimulator, to maintain the efficacy of the therapy.

One or more of the anti-desensitization features described in this disclosure may prevent or delay desensitization while also allowing the patient to initiate the gastric stimulation therapy. A clinician may set the anti-desensitization features when initially programming the gastric stimulation therapy or at any time throughout the duration of therapy. For example, a programmer may present a menu for the clinician to select one or more desired anti-desensitization features to be applied to the stimulator individually or in various combinations. In some embodiments, the patient programmer may permit a patient to control the stimulator to start delivery of gastric stimulation therapy, stop delivery of gastric stimulation therapy, and/or adjust one of more parameters associated with gastric stimulation therapy. In other cases, the patient may have limited control or no control over the gastric stimulation therapy.

The patient programmer and stimulator may operate in a cooperative or complementary manner. The patient programmer may not permit the patient to control the stimulator in violation of the lockout period, therapy window, and/or therapy schedule. Alternatively, the stimulator may deny commands received from the programmer that would violate the lockout period, therapy window, and/or therapy schedule. Even if delivery of stimulation is permitted, consistent with therapy windows, therapy schedules, and lockout periods, the programmer or stimulator may implement a burst pattern variation feature, a multi-site stimulation feature, and/or a burst pattern parameter selection feature as described in this disclosure.

For example, the stimulator may automatically apply the therapy window feature, multi-site stimulation feature, burst pattern variation feature, and/or burst pattern parameter selection feature when delivering stimulation therapy pursuant to a request from the programmer. Alternatively, when the programmer requests therapy, it may further specify application of a therapy window feature, burst pattern variation feature, multi-site stimulation feature, and/or burst pattern parameter selection feature by the stimulator. In some cases, the programmer may specify the particular electrodes, channels, and stimulation parameters to be applied by the stimulator in supporting the therapy window feature, multi-site stimulation feature, and/or a burst pattern parameter selection feature.

The various techniques and features described in this disclosure may be implemented within an external programmer, an external or implantable gastric electrical stimulator, or a combination of both. The external programmer may be a patient programmer that accompanies a patient through a daily routine. Various examples of programmers, stimulators and associated functionality are provided for illustration, but without limitation of the various aspects of the disclosure as broadly embodied and described herein.

FIG. 1 is a schematic diagram illustrating an example implantable gastric stimulation system 10. System 10 is configured to prevent desensitization of a patient 16 to the gastric stimulation therapy. System 10 delivers gastric stimulation therapy to patient 16 in the form of electrical stimulation. Patient 16 may be a human or non-human patient. However, system 10 will generally be described in the context of delivery of gastric stimulation therapy to a human patient, e.g., to treat obesity or gastroparesis. Gastric distention may generally refer to an increase in gastric volume or a relaxation in gastric muscle tone. Hence, a volumetric change associated with gastric distention may be indicative of a state or relaxation of gastric muscle tone. In general, in accordance with this disclosure, gastric distention, increase in gastric volume and relaxation of gastric muscle tone may be used interchangeably to generally refer to a relative state of contraction or relaxation of the stomach muscle.

The state of contraction or relaxation of the stomach muscle may be evaluated using a device called a balloon barostat. The Distender Series II™, manufactured by G&J Electronics, Inc., Toronto, Ontario, Canada, is an example of a balloon barostat system that may be used to diagnose certain gastric motility disorders. Using this system, a balloon is inserted into the stomach, and inflated to a pressure just above the abdominal pressure, referred to as the minimum distending pressure. The barostat is configured so that the pressure in the balloon is maintained at a constant pressure. If the state of contraction of stomach muscle decreases, i.e., the state of relaxation of the stomach muscle increases, then the balloon volume will increase. A decrease in the state of stomach muscle contraction, if measured under conditions of constant balloon pressure, indicates a change in gastric muscle tone, i.e., gastric muscle relaxation, and is sometimes referred to as a change in gastric distention, gastric volume, or gastric tone. More particularly, a decrease in muscle contraction corresponds to an increase in muscle relaxation and promotes distention in terms an increase in gastric volume using balloon barostat evaluation.

Gastric stimulation therapy is generally described herein as being provided to cause gastric distention, which may be associated with an increase in gastric volume and indicate an increase in gastric muscle tone relaxation. Alternatively or additionally, gastric stimulation therapy may be delivered by system 10 to induce nausea, cause regurgitation, or cause other actions to treat certain patient disorders. In other embodiments, gastric stimulation therapy parameters may be selected to induce or regulate gastric motility, while in other embodiments the gastric stimulation therapy parameters are selected not to induce or regulated gastric motility but to promote gastric distention.

Inducing gastric distention in patient 16 causes the volume of stomach 22 to increase, simulating a full or fuller stomach, and causing patient 16 to feel prematurely satiated before or during consumption of a meal. Increased gastric distention and volume are generally consistent with a decreased state of stomach muscle contraction, which conversely may be referred to as an increased state of stomach muscle relaxation. While gastric stimulation therapy is shown in this disclosure to be delivered to stomach 22, the gastric stimulation therapy may be delivered to other portions of patient 16, such as the duodenum or other portions of the small intestine.

As shown in FIG. 1, system 10 may include an implantable stimulator 12 and an external patient programmer 14, both shown in conjunction with a patient 16. Implantable stimulator 12 may be referred to generally as an IMD. Patient programmer 14 and stimulator 12 may communicate with one another to exchange information such as commands and status information via radio frequency (RF) wireless telemetry. Stimulator 12 includes an electrical stimulation generator that generates electrical stimulation pulses or continuous signals. For purpose of illustration, however, and without limitation, pulses will be generally described herein. In some embodiments, system 10 may further include a drug delivery device that delivers drugs or other agents to the patient for obesity or gastric motility therapy, or for other nongastric related therapies. One or more implantable leads 18, 20 carry the electrical stimulation from stimulator 12 to stomach 22. In other embodiments, stimulator 12 may be formed as an RF-coupled system in which an external controller provides both control signals and inductively coupled power to stimulator 12 within patient 16. Also, in alternative embodiments, system 10 may use an external, rather than implanted, stimulator, e.g., with percutaneously implanted leads and electrodes.

Leads 18, 20 each may include one or more electrodes 24, 26 for delivery of the electrical stimulation pulses to stomach 22. In the case of multiple electrodes attached to each lead 18, 20, the multiple electrodes may be referred to as an electrode array. Combinations of two or more electrodes on one or both of leads 18, 20 may form bipolar or multipolar electrode pairs. For example, two electrodes on a single lead may form a bipolar arrangement. Similarly, one electrode on a first lead and another electrode on a second lead may form a bipolar arrangement. Various multipolar arrangements also may be realized. A single electrode 24, 26 on leads 18, 20 may form a unipolar arrangement with an electrode carried on a housing of stimulator 12. Although the electrical stimulation, e.g., pulses or continuous waveforms, may be delivered to other areas within the gastrointestinal tract, such as the esophagus, duodenum, small intestine, or large intestine, delivery of stimulation pulses to stomach 22 will generally be described in this disclosure for purposes of illustration. In the example of FIG. 1, electrodes 24, 26 are placed in lesser curvature 23 of stomach 22. Alternatively, or additionally, electrodes 24, 26 could be placed in the greater curvature of stomach 22 or at some other location around stomach 22.

As mentioned above, gastric distention tends to induce a sensation of fullness and thereby discourages excessive food intake by the patient. The therapeutic efficacy of gastric electrical stimulation in managing obesity depends on the stimulation parameters and stimulation target. Electrical stimulation may have mechanical, neuronal and/or hormonal effects that result in a decreased appetite and increased satiety. In turn, decreased appetite results in reduced food intake and weight loss. Gastric distention, in particular, causes a patient to experience a sensation of satiety due to expansion of the stomach, biasing of stretch receptors, and signaling fullness to the central nervous system.

While electrical stimulation to stomach 22 may cause gastric distention, tissue stimulated by the electrical pulses may not continue to react in substantially the same manner after many pulses are delivered over a period of time. Electrical stimulation to the same tissue over an extended period of time such as hours, days or weeks may decrease the effectiveness of the stimulation to the tissue. In particular, the tissue may become desensitized or accommodating of the stimulation therapy. Therefore, the therapy becomes less effective to the point that patient 16 receives no further benefit from stimulating the same tissue. System 10 may include one or more anti-desensitization features, implemented by programmer 14, stimulator 12, or both. The features may be designed to reduce the extent of desensitization, or prevent or delay desensitization of stimulated tissue. The anti-desensitization features may extend the efficacy of gastric stimulation therapy delivered to the patient.

Reducing desensitization may involve limiting the amount of simulation delivered to a specific tissue of stomach 22 over time. It may not be necessary to provide gastric stimulation therapy throughout the majority of the day for patient. Instead, stimulation therapy may be patient-initiated when patient 16 feels hungry and requires therapy to avoid ingesting excessive calories. In this manner, stimulation therapy may only be delivered to stomach 22 when needed.

One example anti-desensitization feature may be a lockout period that prevents patient programmer 14 from directing stimulator 12 to deliver gastric stimulation therapy upon receiving an indication from patient 16 to start therapy. The lockout period may begin when stimulation therapy begins or when stimulation therapy is turned off. Generally, the lockout period may be between approximately 5 and 240 minutes. More specifically, the lockout period may be between approximately 30 and 120 minutes. The lockout period may vary in duration depending upon the frequency of stimulation, the duration of stimulation, the time of day, patient condition, or other variables that may effect the desired lockout period. For example, the lockout period may be 60 minutes between 7:00 AM and 12:00 PM, 90 minutes between 12:00 PM and 5:00 PM, and 120 minutes between 5:00 PM and 7:00 AM. The lockout periods may also change through the duration of therapy to prevent patient 16 from adapting to the lockout period and circumventing therapy.

In operation, the patient may initiate delivery of electrical stimulation therapy by stimulator 12 via patient programmer 14 for a permitted period of time, which may be referred to as a therapy window W, and which may constitute another type of anti-desensitization feature. The period of time could be, for example, one to two hours to cover an ordinary meal time. In addition, the period of time may be selected based on a therapy window desensitization feature, as described elsewhere in this disclosure. Following a start of the delivery of the gastric electrical stimulation therapy, delivery of the gastric electrical stimulation therapy may be terminated upon expiration of the therapy window. After applying the stimulation therapy for the permitted period of time, patient programmer 14 would institute the lockout period feature such that the patient 16 is prohibited from restarting stimulation for a specified period of time (the lockout period) following termination of electrical stimulation therapy. As an illustration, if stimulation was active for a permitted period of time of one hour, e.g., as specified by a therapy window or otherwise, following termination of the stimulation the patient 16 would not be permitted to restart stimulation for the duration of a lockout period, e.g., 30 to 120 minutes, running from the end of the previous stimulation period.

Patient programmer 14 may be configured to start a clock or other timing device following termination of the electrical stimulation therapy in order to time the lockout period. Once the lockout period has elapsed, patient programmer 14 may permit patient 16 to recommence delivery of electrical stimulation therapy. In particular, if the lockout period is expired, an attempt by the patient 16 to initiate therapy via patient programmer 14 would be successful and the patient programmer would send an appropriate command to stimulator 12 to start therapy. If the attempt is made during the lockout period, however, patient programmer 14 would not send a command to stimulator 12 to start delivery of therapy. Instead, patient programmer 14 may generate a message to the patient 16 indicating that the lockout period is in effect.

As an alternative, stimulator 12 may start a clock or timing device, and be configured to refuse to accept or carry out an additional therapy start command from programmer 14 until a lockout period tracked by such a timing device has expired. Hence, the lockout period feature may be implemented in programmer 14, by refusing to transmit a stimulation start command to stimulator 12 if the stimulation request is received within an active lockout period tracked by the programmer. Alternatively, stimulator 12 may implement the lockout period feature by refusing to start stimulation in response to a stimulation start command from programmer 14 if the command is received within an active lockout period tracked by the stimulator. In this case, the stimulator 12 may receive the request from the patient via an external programmer via wireless telemetry. Stimulator 12 then may communicate the refusal to programmer 14, e.g., by wireless telemetry.

In either case, whether the lockout feature is enforced by stimulator 12 or programmer 14, the programmer 14 may notify the patient 16 that the lockout period is active and that stimulation cannot be restarted. The notification may be communicated by audible, visual, and/or tactile media, such as a speaker, display or buzzer. In some embodiments, programmer 14 may notify the patient 16 of the lockout and advise the patient of the time at which the lockout period will expire. In other cases, programmer 14 may indicate a running time or countdown of the lockout period, e.g., on a display or other user interface feature, which may discourage the patient 16 from even trying to start stimulation during the lockout period. Hence, a user interface of the programmer 14 may indicate at least one of a running time, a countdown, or an expiration time of the lockout period to a user.

With the lockout feature, a external programmer or an implantable gastric electrical stimulator may control delivery of gastric electrical stimulation therapy from an implantable gastric electrical stimulator to a patient for a first period of time, but deny a patient request received by an external programmer to deliver the gastric electrical stimulation therapy from the implantable gastric electrical stimulator to the patient for a second period of time following the first period of time. In this case, the second period of time is the lockout period. The patient request may be received and processed by the patient programmer to impose the lockout period feature. Alternatively, the patient request received by the external programmer may be transmitted to the implantable gastric electrical stimulator, which then processes the request to apply the lockout period feature.

Another example anti-desensitization feature is a therapy window that defines the duration of electrical stimulation. The therapy window may be enforced by stimulator 12, programmer 14, or both. Once gastric stimulation is started, the therapy window may limit the duration of the stimulation to the length of the window in order to limit the amount of stimulation delivered to the tissue. Generally, the therapy window may be between approximately 1 and 60 minutes in duration. More specifically, the therapy window may be between approximately 3 and 30 minutes in duration. Shorter or longer therapy windows may be necessary to treat patient 16, depending upon stimulation parameters and patient condition. Different therapy windows, i.e., of different lengths, may be predetermined for different therapeutic effects and different periods of time for which the therapeutic effects are desired. Accordingly, when a desired therapeutic effect is desired for a particular period of time, the effect and the time can be mapped to an appropriate therapy window that has been predetermined to support the effect and the time. In general, patient programmer 14 may initiate a clock or other timing device to track the running of the therapy window. When the therapy window expires, patient programmer 14 may send a command to stimulator 12 to stop delivery of stimulation therapy. Alternatively, such a clock or timer may be maintained within stimulator 12, such that a stop command from patient programmer 14 is not needed. Instead, stimulator 12 may stop delivery when a clock or timing device within the stimulator indicates that the therapy window has expired.

Patient physiology may support shorter therapy windows in order to further minimize desensitization of tissue in stomach 22. After delivering electrical stimulation to stomach 22 that results in stomach distention, stomach 22 may remain at least partially distended for a residual recovery period of time during which the stomach transitions from a distended state to a normal state. The at least partial distention may be sufficient to retain a feeling of satiety, or other sensation discouraging food intake, in patient 16 during the recovery period. In some cases, it may take stomach 22 between 30 and 60 minutes to recover from the stimulation induced distention and return to a baseline gastric volume level. In other words, the stomach may require 30 to 60 minutes to decrease to a baseline volume from a 50% increased (distended) volume induced by stimulation. Consequently, system 10 may take advantage of this "residual" distention of stomach 22 and deliver stimulation for a duration just long enough to effectively distend the stomach to a desired volume and subsequently turn off the stimulation, relying on the residual distention to effectively treat patient 16 for a longer period of time even though stimulation has been terminated. In this disclosure, the 50% increase is described for purposes of illustration. However, other increase levels or other parameters may be selected as an indication of the desired therapeutic effect. Moreover, other types of desired therapeutic effects, in addition or as an alternative to distention, may be use.

After stimulation is turned off, i.e., upon expiration of the therapy window, the distention may remain above a desired level for a desired period of time, e.g., at or above a 50% increase in gastric volume from a baseline gastric volume, e.g., as would be indicated by a balloon barostat. For example, a desired therapeutic effect may be distention that causes an increase in gastric volume of at least 50% relative to a pre-stimulation baseline value. In this case, 50% serves as a threshold percentage for the desired therapeutic effect. Hence, a delay in post-stimulation recovery to the baseline volume may permit selection of shorter therapy windows while still maintaining desired therapeutic results beyond the expiration of the therapy windows.

In this manner, system 10 may further limit the duration of electrical stimulation and desensitization to the tissue adjacent electrodes 24, 26. Again, a therapy window may be selected to promote stimulation-induced distention of the stomach to a desired volume effective in causing a feeling of satiety, with the knowledge that residual, post-stimulation distention may maintain the feeling of satiety for some time after termination of stimulation. The appropriate length of the therapy window may be selected based on a determination or estimation of a length, i.e., a first period of time, sufficient to achieve a desired therapeutic effect for a desired period of time, i.e., a second period of time.

The second period of time extends beyond the first period of time. In some cases, the second period of time may be greater than the first period of time. In other cases, the second period of time may be less than the first period of time. The second period of time, during which the desired therapeutic effect is maintained, may be inclusive of the first period of time, or overlap with at least a portion of the first period of time, during which stimulation is delivered. The length of the first period of time defining the therapy window may be estimated based on the length of a second period of time in which a typical therapeutic effect is observed for a class of patients. Alternatively, the length of the first period of time may be determined for individual patients and customized based on therapeutic effect measured for such patients.

For an example therapeutic effect of gastric distention that causes an increase in gastric volume from an initial volume, the first and second periods of time both may be on the order of a few minutes to a few hours. For example, the first period of time during which stimulation is delivered may be on the order of a few minutes to several minutes, while the second period of time, which is longer than the first period of time, could be several minutes to a few hours. As one illustration, the first period of time could be approximately five minutes, while the second period of time, due to residual effects, may be approximately 30 to 60 minutes. Alternatively, the first period of time could be approximately one hour while the second period of time is approximately one and one-half hours, depending on the selected stimulation parameters and the physiological response of the patient.

Because battery longevity in an implantable stimulator is a paramount concern, a shorter therapy window defined by the first period of time may also provide a significant benefit in power reduction. Implantation of stimulator 12 in patient 16 requires surgery. Similarly, surgery may be required for explanation of stimulator 12 in the event battery resources are exhausted, as well as for re-implantation of a replacement stimulator. To reduce the number of surgical operations, and associated pain, recovery time, and risks, it is desirable to preserve battery resources to the extent possible while ensuring therapeutic efficacy. Because shorter electrical stimulation durations may reduce power consumption while increasing battery longevity, delivery of gastric stimulation therapy in addition to utilizing the residual distention of stomach 22 to prolong therapeutic effects may achieve therapeutic efficacy in causing gastric distention while promoting battery longevity. Even if a rechargeable battery is used, application of a therapy window feature may be effective in increasing the operating time between charges.

As discussed above, the therapy window may be selected, in some embodiments, as a first period of time during which stimulation must be applied in order to produce therapeutic effects for a desired period of time. This first period of time may be selected as approximately a minimum period of time sufficient to produce the desired therapeutic effect for the second period of time. Accordingly, if the desired therapeutic effect is desired for the second period of time, then the first period of time is selected as approximately the minimum period of time sufficient to support maintenance of the desired therapeutic effect for the second period of time. The first period of time may vary based on the patient and applicable stimulation therapy parameters, such as current or voltage amplitude, pulse rate, pulse width, electrode configuration and the like.

It may be determined or estimated for a particular patient or class of patients that electrical stimulation on the order of x minutes generally produces prolonged therapeutic effects on the order of $z=x+y$ minutes, where y represents the number of minutes for which therapy is deemed effective following termination of the application of stimulation energy during the first period of time x. If the therapeutic effect does not reach a desired level until after stimulation has been delivered for part of the first period of time, e.g., after m minutes, then the second period of time may be equivalent to $z-m$ minutes.

As an example, if the stimulation has parameters selected to cause gastric distention, a physician or other caregiver may determine the parameters and duration of electrical stimulation sufficient to achieve a desired volumetric change in the stomach, as well as the time following termination of stimulation for which the volumetric change remains in effect or remains above a threshold percentage, e.g., 50% above a baseline, pre-stimulation volume. The duration found to be effective in producing the desired volumetric change and maintaining the volumetric change or an acceptable percentage of the volumetric change, e.g., 50%, for a desired, second period of time may then be designated as the therapy window used as the first period of time. The therapy window may change according to the particular parameters applied for electrical stimulation.

Patient programmer 14 or stimulator 12 may use the therapy window to limit the time for which stimulation is applied, while ensuring that a prolonged therapeutic effect, such as gastric distention, is maintained for a desired period of time after cessation of stimulation. Hence, the maximum period of time specified by the therapy window as the first period of time for delivery of stimulation may be selected as the minimum period of time sufficient to produce the desired therapeutic effect for the second period of time, given the residual therapeutic effect that remains following cessation of stimulation. As discussed above, the therapy window may be estimated or determined empirically by clinical evaluation of a particular patient, e.g., by gastric volume analysis during and after application of stimulation for the particular patient or a class of patient.

Hence, upon receiving a request to deliver gastric electrical stimulation therapy, a programmer 14 or stimulator 12 may deliver the gastric stimulation therapy for a first period of time as a therapy window. Delivery of stimulation therapy may be requested by a patient or requested internally within a programmer or stimulator as an automated request, e.g., according to a therapy schedule. Again, the first period of time may be selected as a function of an approximate duration of the gastric electrical stimulation therapy that is effective in producing a desired therapeutic effect for a second period of time. The second period of time for which the desired therapeutic effect is produced may be less than, equal to, or greater than the first period of time. The first period of time that is sufficient to produce the desired therapeutic effect for the second period of time may vary according to selected stimulation parameters and stimulation site. The second period of time may be the overall time for which a desired therapeutic result is achieved.

The first period of time may be greater than or equal to a minimum time for which stimulation is delivered in order to cause the desired therapeutic effect to last for the second period of time. In some cases, a small time margin may be added to this minimum time to produce the first period of time. Accordingly, the first period of time defining the therapy window may be the minimum time or some other time that is selected or determined based on or as a function of the minimum time. To promote anti-desensitization and conserve battery resources, however, it may be desirable to select the first period of time to be approximately a minimum period of time sufficient to produce the desired therapeutic effect for the second period of time. Ordinarily, the first and second periods of time may overlap. The second period of time may subsist for some time following expiration of the first period of time. In other words, the desired therapeutic effect for the second period of time may last for some period of time after delivery of electrical stimulation therapy has ceased. The first period of time limits the duration of delivery of stimulation to the patient. The second period of time is the time for which a desired therapeutic effect produced by the stimulation remains in effect.

The desired therapeutic result may be a physiological response such as a degree of gastric distention, i.e., which may correlated with a degree of gastric relaxation. A degree of gastric distention may be measured in terms of an increase in a gastric volume that is at least 50% above a baseline or pre-stimulation level, i.e., a level of gastric volume prior to application of electrical stimulation. The 50% level is used for purposes of illustration. Other target levels may also be specified, such as 35% or 65% above baseline levels. For example, before gastric electrical stimulation is applied, a baseline gastric volume may be measured with a balloon barostat. Upon delivery of gastric stimulation, gastric volume begins to increase to a preselected gastric volume target level of 50% above the baseline gastric volume level. Other target levels less than or greater than 50% may be specified, as mentioned above, depending on the needs of the patient. Upon termination of gastric stimulation, gastric volume may slowly decay from the target level to the initial baseline level, pre-stimulation level, or some other level. The time during which gastric volume is at or greater than the target level may be considered to be the second period of time during which the desired therapeutic effect is maintained.

The amount of time that the gastric volume is above the target level is the time during which the desired therapeutic effect is maintained, and may be determined as follows. After insertion of a barostat balloon into the stomach of a patient, and adjusting the balloon pressure to a level above the abdominal pressure at time t0, a baseline stomach volume may be determined. Upon initiating gastric stimulation at time t1, gastric volume begins to increase, reaching the example target level of 50% above baseline at time t2, and the maximum volume at time t3. The target level of 50% above baseline volume may be referred to as the therapeutic threshold.

After delivery of gastric electrical stimulation is discontinued at time t4, gastric volume may decline over time, decreasing to 50% above baseline by time t5, and returning to baseline levels by time t6. The therapy window T1 (=t4–t1) indicates the time during which electrical stimulation is delivered. The second period of time T2 (=t5–t2) that the gastric volume remains above the therapeutic level, i.e., producing the desired therapeutic effect, generally extends beyond the stimulation time T1, i.e., the first period of time or therapy window, during which stimulation is applied. The overall second period of time T2 may be greater than or less than the stimulation time T1.

The actual times T1 and T2 may be measured in animals or humans using devices and techniques well known in the field of gastroenterology, including the balloon barostat. Other techniques or devices which assess the state of tonic muscle contraction in the stomach may also be used to determine the first and second periods of time T1 and T2 including those that measure changes in length or thickness of a segment of the stomach using ultrasound, mechanical, optical, magnetic, or other electronic transducers.

As an illustration, the result may be a therapy window that permits delivery of stimulation within a therapy window of 5 minutes, with a prolonged effect of 30 minutes after cessation of stimulation. Hence, therapy may be delivered for only a first period of time T1 of approximately 5 minutes to achieve an overall desired therapeutic effect over a second period of time T2 of approximately 35 minutes (or somewhat less than 35 minutes in the event the desired therapeutic effect is not immediately produced upon application of stimulation), which may be inclusive of the first period of time or a portion of the first period of time. The second period of time may overlap with the first period of time, but subsist for some period of time after cessation of delivery of stimulation. In other words, the second period of time extends at least in part beyond an end of the first period of time. In this manner, stimulator 12 only needs to deliver stimulation for a first period of time T1 that is long enough to ensure a desired therapeutic effect over a desired second period of time T2.

By delivering stimulation for a first period of time selected to produce a therapeutic effect for a second, desired period of time, rather than delivering stimulation for the entire desired period of time for the therapeutic effect, a stimulator may reduce power consumption and reduce desensitization that may result from prolonged delivery of stimulation. The ratio of the length of the therapy window to the length of time that the desired therapeutic effect remains substantially intact may vary according to the type of therapeutic effect, the patient, the stimulation parameters used to deliver the stimulation, electrode configuration, stimulation target site, or other factors.

As another anti-desensitization feature, patient programmer 14, stimulator 12, or both may only permit stimulation to be delivered according to a therapy schedule that specifies times during which stimulation is permitted. Such times may be, for example, approximately one to three hour windows selected at or around ordinary meal times or snack times. For example, patient programmer 14 may be configured to permit therapy delivery during time periods corresponding to ordinary breakfast, lunch and dinner times, as well as snack times, if necessary. A therapy window specifying the maximum continuous time for which stimulation may be delivered may be placed at different temporal positions within such a time period.

In this manner, when a patient attempts to activate stimulation, patient programmer 14 may determine whether the activation request is made within one of the permitted time periods on the therapy schedule. If so, patient programmer 14 transmits a command to stimulator 12 to cause the stimulator to deliver therapy, possibly subject to other desensitization features, such as lockout period and therapy window features, e.g., as described above. If the request is not made within a permitted time period on the therapy schedule, patient programmer 14 does not send a command to stimulator 12 to initiate therapy, and instead may generate a notification advising the patient 16 that therapy is not permitted at the requested time.

As an alternative, stimulator 12 may be responsible for maintaining the therapy schedule feature. In this case, programmer 14 may transmit a command to start electrical stimulation therapy in response to a patient request. If stimulator 12 receives the command from programmer 14 within a permitted period of time on the therapy schedule, it may deliver stimulation. Delivery of stimulation may be subject to other anti-desensitization features such as lockout period and therapy window. If stimulator 12 receives the command from programmer 14 at a time that is not within a permitted period of time on the therapy schedule, stimulator refuses to deliver stimulation and may transmit a message notifying programmer 14 of such refusal, in which case the programmer may generate a notification for the patient 16.

The therapy schedule may be the same every day. To further prevent or delay desensitization, however, the therapy schedule maintained by programmer 14 and/or stimulator 12 may be adjusted to vary the start times for the permitted periods of time, e.g., by minutes or hours. Hence, variation of the start time of the gastric stimulation throughout therapy may provide another anti-desensitization feature. When stimulation is delivered to a specific tissue site at the same time every day, the tissue site may become desensitized to the stimulation as the tissue becomes accustomed to the routine stimulation. In addition, a patient 16 may adjust his behavior due to routine stimulation by ignoring the stimulation or changing behavior around the routine stimulation start times. Therefore, beginning stimulation at varying start times may help to reduce desensitization.

Different start times may be used every day, week, month, or at any time during therapy. The start times may vary by minutes or hours, as indicated above. Variation of the stimulation start times may be accomplished by programmer 14 or stimulator 12 by cycling through multiple start times that have been pre-programmed by the clinician. In other cases, stimulator 12 or programmer 14 may randomly select a start time for each delivery of stimulation, possibly subject to some constraints. For example, stimulator 12 or programmer 14 may select a random start time within a preprogrammed range or the randomized start times may be weighted around a target start time.

In the case of weighted randomized start times, stimulator 12 may vary start times while still starting stimulation at some time near the target start time desired by the clinician and/or patient 16. The weighting may be varied during therapy as well in order to further vary start times or accommodate a changing patient schedule. In general, it may be desirable that the therapy schedule conform to meal and snack times. Therefore, permitted periods of time and associated start times on the therapy schedule may vary but still be close to meal and snack times for the patient. As an illustration, a permitted period of therapy associated with lunch may have a permitted start time that varies from 11:30 one day, 12:00 the next day, and 11:45 the next day. As a further measure, stimulator 12 or programmer 14 may be configured to vary end times of permitted periods of time during which stimulation may be applied.

Alternatively, or additionally, multi-site stimulation may be provided as an anti-desensitization feature to vary the location of electrical stimulation to extend efficacious therapy of stomach 22. Multiple electrodes may be located on stomach 22 and connected to stimulator 12. For example, electrodes 24, 26 may be electrode arrays in which stimulator 12 may selectively activate one or more electrodes of the arrays during therapy to select different electrode combinations. The electrode combinations may be associated with different positions on the stomach or other gastrointestinal organ. For example, the electrodes combinations may be located at the different positions or otherwise positioned to direct stimulation to the positions. In this manner, different electrode combinations may be selected to deliver stimulation to different tissue sites. The selection of electrodes forming an electrode combination used for delivery of electrical therapy at one time may change to a different selection of electrodes forming an electrode combination for delivery of electrical therapy at a different time. The selection may vary between each delivery of stimulation or a predetermined number of delivery periods or total amount of delivery time.

In general, to implement the multi-site feature for anti-desensitization, a programmer or stimulator may cause delivery of first electrical stimulation therapy to a gastrointestinal organ of a patient via a first electrode combination associated with a first position on the gastrointestinal organ for a first period of time, and delivery of second electrical stimulation therapy to the gastrointestinal organ via a second electrode combination associated with a second position on the gastrointestinal organ for a second period of time. The first and second electrical stimulation therapies are configured to produce a substantially identical therapeutic result. The different electrode combinations may provide different stimulation channels. As an example, stimulation delivered via the first and second channels may be configured to produce gastric distention, nausea or discomfort to discourage food intake by the patient. In some cases, the stimulation may be configured to regulate gastric motility. In other cases, the stimulation may be configured to not regulate motility, and instead promote distention, nausea or discomfort.

A first electrode combination may include electrodes implanted at one location on the stomach, or elsewhere in the gastrointestinal tract, and the second electrode combination may include electrodes implanted at a different location. In this manner, the stimulation therapy is delivered to two or more different tissue sites. The first and second electrode combinations may be implanted in the same gastrointestinal organ. For example, the first and second electrode combinations may both be implanted in the stomach, or may both be implanted in the intestine. Each electrode combination may comprise two or more electrodes, which may be provided on one or more implantable leads. In some cases, an electrode combination may include the device housing or can as an electrode.

Each of first and second periods of time may be greater than or equal to approximately 30 seconds, greater than or equal to one minute, greater than or equal to five minutes, greater than or equal to ten minutes, greater than or equal to one hour, or greater than or equal to one day. The first and second periods of time may partially overlap or not overlap with one another.

The first and second periods of time for which stimulation is delivered to first and second electrode combinations, respectively, may be equal to or different from one another. In general, the first and second periods of time will not be coextensive.

By delivering stimulation to different electrode combinations at different tissue sites at different times, desensitization of one tissue site may be reduced. As the first and second periods of time are lengthened, however, a single tissue site may be exposed to stimulation for an extended period of time. Accordingly, shorter periods of time on the order of seconds, minutes, hours or days may be desirable, e.g., in contrast to weeks or months. Over the potentially lengthy operational life of a stimulator, however, delivering stimulation via one electrode combination for weeks or months followed by switching delivery to a second electrode combination for weeks or months may still be desirable.

When the selection of electrode combination is changed, e.g., from the first period of time to a second period of time, patient programmer 14 or stimulator 12 may determine the next selection of electrodes based upon instructions defined by a clinician. The instructions may direct the selection to progressively move to the next set of electrodes in an electrode array, move to the next electrodes that retain the desired distance or orientation between electrodes, or randomly select the next electrodes to use for delivery of therapy. In the case of randomized selection of electrodes, a new selection may be different than the previous selection to avoid continued electrical stimulation exposure to the same tissues. Stimulator 12 and/or patient programmer 14 may store each selection of electrodes used during the course of gastric stimulation therapy so that a clinician may review the selections and identify any potential problems with the changing electrodes or ineffective therapy with one or more electrodes being used.

In some cases, a multi-site stimulation feature may make use of three or more electrode combinations. For example, a programmer or stimulator may further cause delivery of third electrical stimulation therapy to the gastrointestinal organ via a third electrode combination associated with a third position on the gastrointestinal organ at a third time, repeat the delivery of the first, second and third electrical stimulation therapies for the first, second and third periods of time, and select an order of the first, second and third periods of time in a varying order for at least some of the repeated deliveries. For example, in some cases, stimulation via the first, second, and third electrode combinations may proceed in that order. Alternatively, stimulation could proceed from first, to third, to second electrode combination, from third, to second, to first electrode combination, from third, to first, to second electrode combination, or in other orders. The first, second and third electrical stimulation therapies may be configured to produce a substantially identical therapeutic result. In some cases, the first, second and third positions are arranged such that the first position is most proximal on the gastrointestinal organ, the third position is most distal on the gastrointestinal organ, and the second position is between the first and third positions, where proximal refers to portions closer to the start of the gastrointestinal tract and distal refers to portions closer to the end of the gastrointestinal tract.

For example, first and second electrode sets used to form first and second electrode combinations, respectively, may be displaced from one another by at least approximately 1 cm, more preferably at least approximately 3 cm, and still more preferably at least approximately 5 cm. In some cases, the electrode combinations may be associated with positions that are greater than 10 cm apart. As an illustration, the different electrode sets could each be implanted within the lesser curvature of the stomach, but displaced approximately 5 cm from one another. In this manner, the different electrode combinations are positioned to deliver stimulation to different tissue sites, and thereby delay or reduce likelihood of desensitization of a given tissue stimulation site. In general, first and second electrode sets may be implanted a sufficient distance away from one another such that they tend to activate different tissue sites, or otherwise be implanted to deliver stimulation to tissue sites that are positioned a sufficient distance away from one another. The first and second electrode combinations may be placed at different positions on the same organ, such as different positions on the stomach or different positions on the small intestine. Alternatively, or additionally, the first and second electrode combinations may be placed at different positions on different organs, e.g., at one position on the stomach and another position on the small intestine.

Stimulator 12 and/or programmer 14 may control the stimulator to deliver stimulation via two or more different electrode combinations on a time-interleaved or time-independent basis. For example, stimulation may be delivered via different electrode combinations on a time-interleaved basis in different time slots, e.g., within a given therapy window or period of time on the therapy schedule. In this case, two or more stimulation channels may be active and controlled to deliver stimulation in respective time slots, which may partially overlap or not overlap. In this case, stimulation at different electrode combinations may be delivered together within a therapy window, but on a time-interleaved basis. Alternatively, stimulation may be delivered via different electrode combinations in separate therapy windows, such that each electrode combination is used separately and independently of one another. In this case, only one channel may be active at a time and may not coordinate timing with another channel within a given therapy window.

As described above, stimulator 12 may include a first channel coupled to a first set of electrodes forming a first electrode combination and a second channel coupled to a second set of electrodes forming a second electrode combination. Additional channels, such as a third channel coupled to a third set of electrodes, may be provided in some embodiments. Individual electrodes in the sets of electrodes may be selected to form electrode combinations, either among the electrodes or among one or more electrodes and an electrode surface on a housing of the stimulator. Stimulator 12 may be configured to deliver stimulation with identical, similar or different parameters via the first and second channels to achieve a substantially identical therapeutic effect.

As another anti-desensitization feature, programmer 14 and/or stimulator may apply a burst pattern parameter selection feature to vary the characteristics of stimulation delivered to patient 16. For example, the burst pattern parameter selection feature may include varying stimulation parameters of pulses within bursts of pulses delivered to patient 16. In one example, the stimulation parameters may be varied between at least two pulses within a single burst of pulses. Therefore, not all the pulses within a given burst have the same stimulation parameters. In another case, the stimulation parameters may be varied between the pulses of successive bursts of pulses. This variation of stimulation parameters allows for each burst to have identical pulses while the pulses of subsequent bursts may be different. Additionally, the parameter selection feature may specify that a combination of pulses are varied within a burst and between subsequent bursts.

As a further alternative, pulses may be delivered in burst patterns, where each pattern contains multiple pulse bursts. In this case, pulse parameters may be varied among different burst patterns. For example, first pulses in bursts associated with a first burst pattern may have identical pulse parameters, while second pulses in bursts associated with a second burst pattern may have one or more pulse parameters that are different from pulse parameters associated with the first pulses in the first burst pattern. Hence, successive burst patterns may have one or more different pulse parameters. Alternatively, pulses within bursts in a first burst pattern may be varied relative to one another, and relative to pulses within bursts in a second burst pattern. In addition, timing of bursts in different burst patterns may be varied.

The variation of stimulation parameters between pulses may be of slight magnitude so that the stimulation pulses are not constantly the same without drastically changing the efficacy of the stimulation therapy as a whole. In other words, the variation in stimulation parameters may be only directed to have an effect upon the desensitization of the tissue and not the overall effect of the perceived therapy. For example, a stimulation parameter change from a previous pulse to a subsequent pulse may differ by less than approximately ten percent, or less than approximately five percent. However, the stimulation parameters may change by more than approximately ten percent in some cases where stimulation efficacy is not affected by the larger magnitude changes.

The stimulation parameters that may be varied for the desensitization measure may be current amplitude, voltage amplitude, pulse width, pulse rate, and/or duty cycle. One or more stimulation parameters may be varied at any given time, as long as the stimulation therapy remains effective in treating patient 16. The progression of variation of the stimulation parameter changed to prevent tissue desensitization may be selected by the clinician during therapy programming. The stimulation parameter may cycle between preset parameter values specified by the clinician, vary randomly between a minimum limit and a maximum limit, vary with a weighted randomization that is centered to a target or programmed parameter value, or vary in some other way specified by the clinician. In any case, stimulator 12 may implement an anti-desensitization feature that varies the stimulation parameters over the course of therapy in order to extend the efficacy of gastric stimulation therapy.

System 10 may implement more than one anti-desensitization feature at any given time. For example, system 10 may implement the lockout period after the therapy window has elapsed. In addition, the lockout period and therapy window may be subject to the therapy schedule, and vice versa. In another example, system 10 may implement the lockout period in addition to ordered, randomized, or pseudo-randomized selection of electrodes to vary the location of electrical stimulation periodically throughout therapy. In any case, the anti-desensitization feature used by system 10 may be effective in extending therapy efficacy by reducing or preventing tissue desensitization that shortens the useful life of electrical stimulation therapy. The term "pseudo-random" may generally refer to a quasi random or effectively random output generated by a system, such as software running on a microprocessor (e.g., random number generators), and may be limited to a predetermined range of values.

Stimulator 12 delivers electrical stimulation according to stimulation parameters stored within stimulator 12. In one example, stimulator 12 delivers stimulation pulses with a pulse width selected to promote gastric distention and/or modulate gastric motility. A pulse width in a range of approximately 1 milliseconds to approximately 50 milliseconds, more preferably in a range of approximately 1.5 milliseconds to approximately 10 milliseconds, more preferably approximately 2 milliseconds to approximately 10 milliseconds, and even more preferably approximately 2 to 5 milliseconds, may be effective in causing gastric distention while promoting better power conservation. As an example, the stimulation pulses delivered by stimulator 12 may have a pulse width greater than or equal to approximately 1 millisecond (ms), but generally less than approximately 10 ms. More specifically, the pulse width may be between approximately 2 ms and 5 ms. Pulse widths in this range may be long enough to promote gastric distention but short enough that patient 16 does not generally perceive significant negative effects from the stimulation, e.g., nausea, or cause excessive power consumption.

In another example, stimulator 12 may be programmed to produce feelings of nausea to limit the desire of patient 16 to eat. In this case, pulse widths may be generally greater than approximately 0.5 ms and as long as approximately 50 ms. In still another example, stimulator 12 may deliver pulses with a pulse width greater than approximately 2 ms to reduce motility. In this case, the pulse width may be between approximately 1 ms and approximately 100 ms. Other pulse widths may be used for additional therapy outcomes. The clinician may program the stimulation parameters, such as the pulse width, amplitude, pulse rate, electrode combinations and polarities, upon implant of stimulator 12 and possibly in subsequent clinic visits, in order to appropriately treat the condition of patient 16.

With further reference to FIG. 1, at the outer surface of stomach 22, e.g., along the lesser curvature 23, leads 18, 20 penetrate into tissue such that electrodes 24 and 26 are positioned to deliver stimulation to stomach 22. As mentioned above, the parameters of the stimulation pulses generated by stimulator 12 may be selected to distend stomach 22 and thereby induce a sensation of fullness, i.e., satiety. In some embodiments, the parameters of the stimulation pulses also may be selected to induce a sensation of nausea. In each case, the induced sensation of satiety and/or nausea may reduce a patient's desire to consume large portions of food. Alternatively, the parameters may be selected to regulate motility, e.g., for gastroparesis. Again, the stimulation pulses may be delivered elsewhere within the gastrointestinal tract, either as an alternative to stimulation of lesser curvature 23 of stomach 22, or in conjunction with stimulation of the lesser curvature of the stomach. As one example, stimulation pulses could be delivered to the greater curvature of stomach 22 located opposite lesser curvature 23.

For obesity therapy, the pulse width and/or other parameters may be selected so that electrical stimulation, when applied, causes at least approximately a twenty-five percent increase in gastric volume relative to a baseline gastric volume, preferably at least approximately a thirty-five percent increase in gastric volume, more preferably at least approximately fifty percent increase in gastric volume, more preferably at least approximately a sixty-five percent increase in gastric volume, more preferably at least approximately a seventy-five percent increase in gastric volume, and still more preferably at least approximately a one-hundred percent increase in gastric volume. The increase in gastric volume may be measured relative to a baseline gastric volume, such as a preprandial (pre-meal) and/or pre-stimulation gastric volume, and may be measured within a selected area of the gastrointestinal tract. For example, the gastric volume may be measured within the stomach if electrical stimulation is applied to the stomach. Alternatively, the baseline and stimulation-induced gastric volume may be measured elsewhere within the gastrointestinal tract if electrical stimulation is applied elsewhere.

In addition to pulse width, the stimulation pulses are defined by other parameters including current or voltage amplitude, pulse rate, and duty cycle. In some embodiments, stimulation parameters may further include electrode combinations and polarities in the event leads 18, 20 provide multiple electrode positions. As an illustration, in addition to a pulse width in the ranges identified above, stimulator 12 may generate stimulation pulses having a current amplitude in a range of approximately 1 to 20 milliamps (mA), preferably approximately 2 to 10 mA, and more preferably approximately 3 to 6 mA. An example voltage may be between approximately 0.5 volts and 10 volts. The pulse rate of the stimulation pulses may be in a range of approximately 0.05 to 50 Hertz (Hz), preferably approximately 1 to 50 Hz, more preferably approximately 10 to 50 Hz, and more preferably approximately 20 to 50 Hz. As an illustration, a substantial amount of distention may be produced with a pulse width of approximately 2 ms in combination with a pulse rate of approximately 40 Hz.

In addition, in some embodiments, stimulator 12 may deliver stimulation pulses with a duty cycle of approximately 50% ON/50% OFF, preferably 30% ON/70% OFF, and more preferably 20% ON/80% OFF. The pulses may be generated in bursts, and the bursts may be generated in burst patterns containing multiple bursts. Duty cycle generally refers to the percentage of time that stimulator 12 is delivering stimulation pulses versus the percentage of time during which the stimulator is idle, i.e., not delivering pulses. During ON time, stimulator 12 delivers pulses according to a set of parameters such as amplitude, pulse rate and pulse width. During OFF time, stimulator 12 does not deliver stimulation pulses to patient 16.

In addition, the duty cycle may include the amount of time stimulation pulses are delivered and the amount of time pulses are not delivered to patient 16 when the stimulator 12 is ON. Additionally, a higher level duty cycle includes the amount of time stimulator 12 is ON and OFF. In this manner, example stimulation therapy may have duty cycles that describe when stimulator 12 is ON and OFF in addition to cycles that describe the amount of time pulses are delivered to patient 16 during the ON period. Stimulator 12 may also have nested duty cycles, such as can be defined as bursts of pulses during an ON period of stimulation. Bursts of pulses and burst patterns will be further discussed below.

As one illustration, to cause gastric distention, stimulator 12 may deliver stimulation pulses with an amplitude of approximately 1 to 10 mA, a pulse width of approximately 2 to 10 milliseconds (ms), a pulse rate of approximately 1 to 60 Hz, and a duty cycle of approximately 25% ON/75% OFF. As another illustration, stimulator 12 may deliver stimulation pulses with an amplitude of approximately 3 to 6 mA, a pulse width of approximately 2 to 5 milliseconds (ms), a pulse rate of approximately 20 to 50 Hz, and a duty cycle of approximately 40% ON/60% OFF. Such pulses may be delivered as bursts or burst patterns containing multiple bursts. In each case, stimulator 12 may cause substantial gastric distention and a sensation of fullness, which may result in reduced food intake and, ultimately, weight loss.

Implantable stimulator 12 may be constructed with a biocompatible housing, such as titanium, stainless steel, or a polymeric material, and is surgically implanted within patient 16. The implantation site may be a subcutaneous location in the side of the lower abdomen or the side of the lower back. Stimulator 12 is housed within the biocompatible housing, and includes components suitable for generation of electrical stimulation pulses. Stimulator 12 may be responsive to patient programmer 14, which generates control signals to adjust stimulation parameters. As a further embodiment, stimulator 12 may be formed as an RF-coupled system in which an external controller such as patient programmer 14 or another device provides both control signals and inductively coupled power to an implanted pulse generator.

Electrical leads 18 and 20 are flexible and include one or more internal conductors that are electrically insulated from body tissues and terminated with respective electrodes 24 and 26 at the distal ends of the respective leads. The leads may be surgically or percutaneously tunneled to stimulation sites on stomach 22. The proximal ends of leads 18 and 20 are electrically coupled to the pulse generator of stimulator 12 via internal conductors to conduct the stimulation pulses to stomach 22 via electrodes 24, 26.

Leads 18, 20 may be placed into the muscle layer or layers of stomach 22 via an open surgical procedure, or by laparoscopic surgery. Leads also may be placed in the mucosa or submucosa by endoscopic techniques or by an open surgical procedure. Electrodes 24, 26 may form a bipolar pair of electrodes. Alternatively, stimulator 12 may carry a reference electrode to form an "active can" arrangement, in which one or both of electrodes 24, 26 are unipolar electrodes referenced to the electrode on the pulse generator. The housing of implantable stimulator 12 may itself serve as a reference electrode for the active can arrangement. A variety of polarities and electrode arrangements may be used. Each lead 18, may carry a single electrode or an electrode array of multiple electrodes, permitting selection of different electrode combinations, including different electrodes in a given electrode array, and selection of different polarities among the leads for delivery of stimulation.

In addition to pulse width, as discussed above, the stimulation pulses delivered by implantable stimulator 12 are characterized by other stimulation parameters such as a voltage or current amplitude and pulse rate. Pulse width and the other stimulation parameters may be fixed, adjusted in response to sensed physiological conditions within or near stomach 22, or adjusted in response to patient or physician input entered via patient programmer 14. For example, in some embodiments, patient 16 may be permitted to adjust stimulation amplitude, pulse width, or pulse rate and turn stimulation ON and OFF via patient programmer 14.

Patient programmer 14 transmits instructions to stimulator 12 via wireless telemetry. Accordingly, stimulator 12 includes telemetry interface electronics to communicate with patient programmer 14. Patient programmer 14 may be a small, battery-powered, portable device that accompanies patient 16 throughout a daily routine. Patient programmer 14 may have a simple user interface, such as a button or keypad, and a display or lights. Patient programmer also may include any of a variety of audible, visual, graphical or tactile output media. Patient programmer 14 may be a hand-held device configured to permit activation of stimulation and adjustment of stimulation parameters.

Alternatively, patient programmer 14 may form part of a larger device including a more complete set of programming features including complete parameter modifications, firmware upgrades, data recovery, or battery recharging in the event stimulator 12 includes a rechargeable battery. Patient programmer 14 may be a patient programmer, a physician programmer, or a patient monitor. In some embodiments, patient programmer 14 may be a general purpose device such as a cellular telephone, a wristwatch, a personal digital assistant (PDA), or a pager.

Electrodes 24, 26 carried at the distal ends of lead 18, 20, respectively, may be attached to the wall of stomach 22 in a variety of ways. For example, the electrode may be formed as a gastric electrode that is surgically sutured onto the outer wall of stomach 22 or fixed by penetration of anchoring devices, such as hooks, needles, barbs or helical structures, within the tissue of stomach 22. Also, surgical adhesives may be used to attach the electrodes. In some cases, the electrodes 24, 26 may be placed in the lesser curvature 23 on the serosal surface of stomach 22, within the muscle wall of the stomach, or within the mucosal or submucosal region of the stomach. Alternatively, or additionally, electrodes 24, 26 may be placed in the greater curvature of stomach 22 such that stimulation is delivered to the greater curvature.

In some embodiments, system 10 may include multiple stimulators 12 or multiple leads 18, 20 to stimulate a variety of regions of stomach 22. Stimulation delivered by the multiple stimulators may be coordinated in a synchronized manner, or performed without communication between stimulators. Also, the electrodes may be located in a variety of sites on the stomach, or elsewhere in the gastrointestinal tract, dependent on the particular therapy or the condition of patient 16. Stimulation delivered by the multiple stimulators may be coordinated in a synchronized manner, or performed independently without communication between stimulators. As an example, one stimulator may control other stimulators by wireless telemetry, all stimulators may be controlled by patient programmer 14, or the stimulators may act autonomously subject to parameter adjustment or downloads from patient programmer 14.

Figure 2:
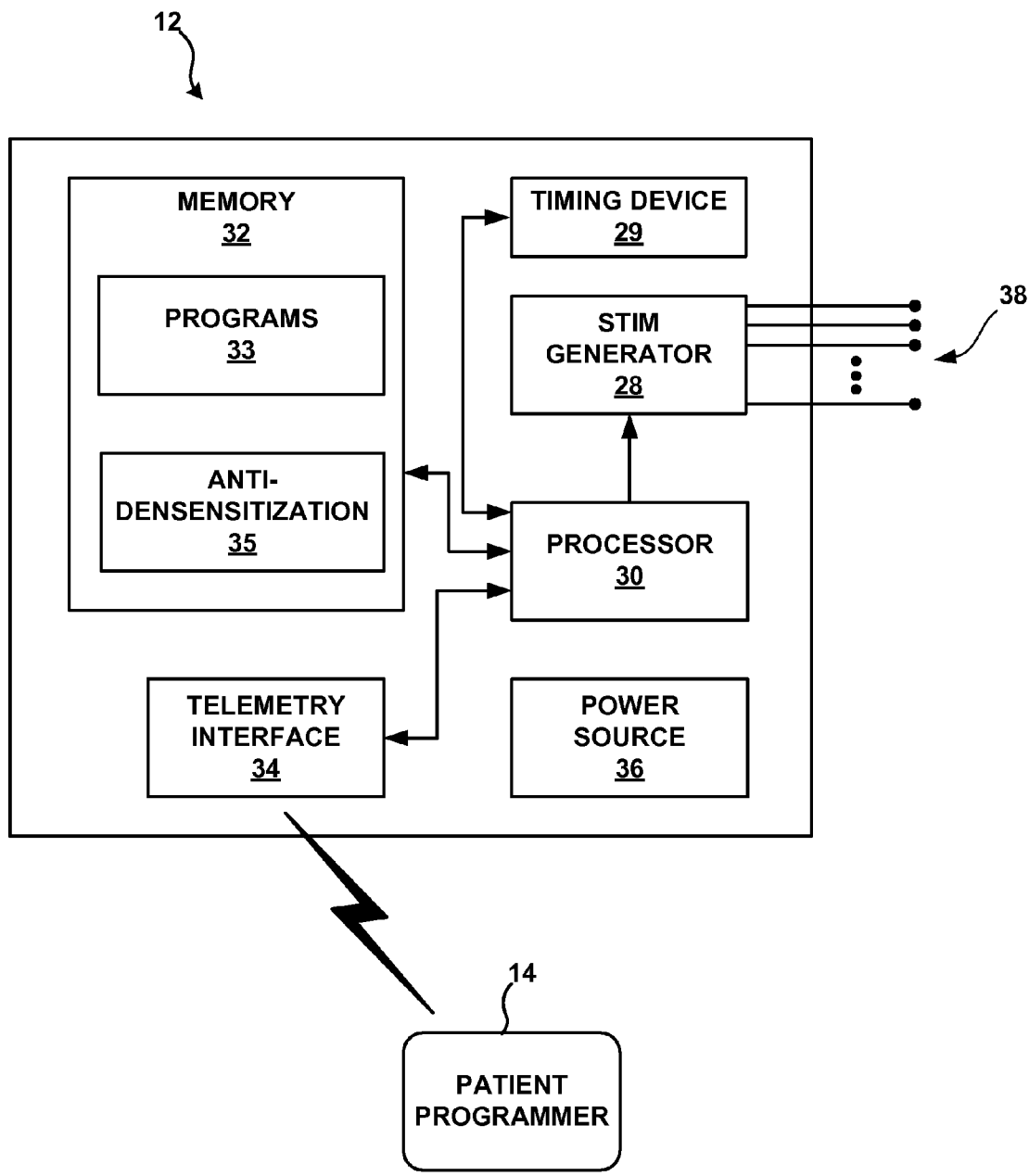
FIG. 2 is a block diagram illustrating example components of an implantable gastric electrical stimulator that delivers gastric electrical stimulation therapy.

FIG. 2 is a block diagram illustrating example components of a stimulator 12 that delivers gastric stimulation therapy to patient 16. In the example of FIG. 2, stimulator 12 includes stimulation generator 28, processor 30, memory 32, wireless telemetry interface 34 and power source 36. In some embodiments, stimulator 12 may generally conform to the Medtronic Itrel 3 Neurostimulator, manufactured and marketed by Medtronic, Inc., of Minneapolis, Minn. However, the structure, design, and functionality of stimulator 12 may be subject to wide variation without departing from the scope of the disclosure as broadly embodied and described in this disclosure.

Processor 30 controls stimulation generator 28 by setting and adjusting stimulation parameters such as pulse amplitude, pulse rate, pulse width and duty cycle, in the case that stimulation generator 28 generates pulses. Alternative embodiments may direct stimulation generator 28 to generate continuous electrical signals, e.g., a sine wave. Processor 30 may be responsive to parameter adjustments or parameter sets received from patient programmer 14 via telemetry interface 34. Hence, patient programmer 14 may program stimulator 12 with different sets of operating parameters. In some embodiments, stimulation generator 28 may include a switch matrix. Processor 30 may control the switch matrix to selectively deliver stimulation pulses from stimulation generator 28 to different electrodes 38 carried by one or more leads 18, 20 (FIG. 1). In some embodiments, stimulator 12 may deliver different stimulation programs to patient 16 on a time-interleaved basis with one another.

Memory 32 stores instructions for execution by processor 30, including operational commands and programmable parameter settings. Example storage areas of memory 32 may include instructions associated with therapy programs 33 and anti-desensitization features 35. Programs 33 may include each program used by stimulator 12 to define parameters and electrode combinations for gastric stimulation therapy. Anti-desensitization features 35 may include instructions for application of one or more anti-desensitization features, as described in this disclosure, such as when to start and stop a lockout period, therapy window durations, therapy schedules, burst pattern variation parameters, multi-site stimulation parameters, electrode selection orders or functions, and burst pattern parameter selection instructions.

Processor 30 may access a clock or other timing device 29 within stimulator 12 to determine pertinent times, e.g., for enforcement of therapy schedules, lockout periods, and therapy windows, and may synchronize such times with times maintained by patient programmer 14. Memory 32 may include one or more memory modules constructed, e.g., as random access memory (RAM), read-only memory (ROM), non-volatile random access memory (NVRAM), electrically erasable programmable read-only memory (EEPROM), and/or FLASH memory. Processor 30 may access memory 32 to retrieve instructions for control of stimulation generator 28 and telemetry interface 34, and may store information in memory 32, such as operational information.

Wireless telemetry in stimulator 12 may be accomplished by radio frequency (RF) communication or proximal inductive interaction of implantable stimulator 12 with patient programmer 14 via telemetry interface 34. Processor 30 controls telemetry interface 34 to exchange information with patient programmer 14. Processor 30 may transmit operational information and receive stimulation parameter adjustments or parameter sets via telemetry interface 34. Also, in some embodiments, stimulator 12 may communicate with other implanted devices, such as stimulators or sensors, via telemetry interface 34.

Power source 36 delivers operating power to the components of implantable stimulator 12. Power source 36 may include a battery and a power generation circuit to produce the operating power. In some embodiments, the battery may be rechargeable to allow extended operation. Recharging may be accomplished through proximal inductive interaction between an external charger and an inductive charging coil within implantable stimulator 12. In other embodiments, an external inductive power supply may transcutaneously power implantable stimulator 12 whenever stimulation therapy is to occur.

Implantable stimulator 12 is coupled to electrodes 38, which may correspond to electrodes 24 and 26 illustrated in FIG. 1, via one or more leads 18, 20. Implantable stimulator 12 provides stimulation therapy to the gastrointestinal tract of patient 16. Stimulation generator 28 includes suitable signal generation circuitry for generating a voltage or current waveform with a selected amplitude, pulse width, pulse rate, and duty cycle. In general, as described in this disclosure, the electrical stimulation and stimulation pulses generated by stimulation generator 28 may be formulated with pulse widths and appropriate times suitable to cause substantial gastric distention without excessive consumption of power provided by power source 36.

In the example of FIGS. 1 and 2, stimulator 12 includes leads 18, 20. In other embodiments, stimulator 12 may be a leadless stimulator, sometimes referred to as a microstimulator, or combination of such stimulators. In this case, the housing of stimulator 12 may include multiple electrodes to form electrode combinations for delivery of stimulation to the stomach, intestines, or other organs within patient 16. In additional embodiments, stimulator 12 may include three of more leads.

Figure 3:
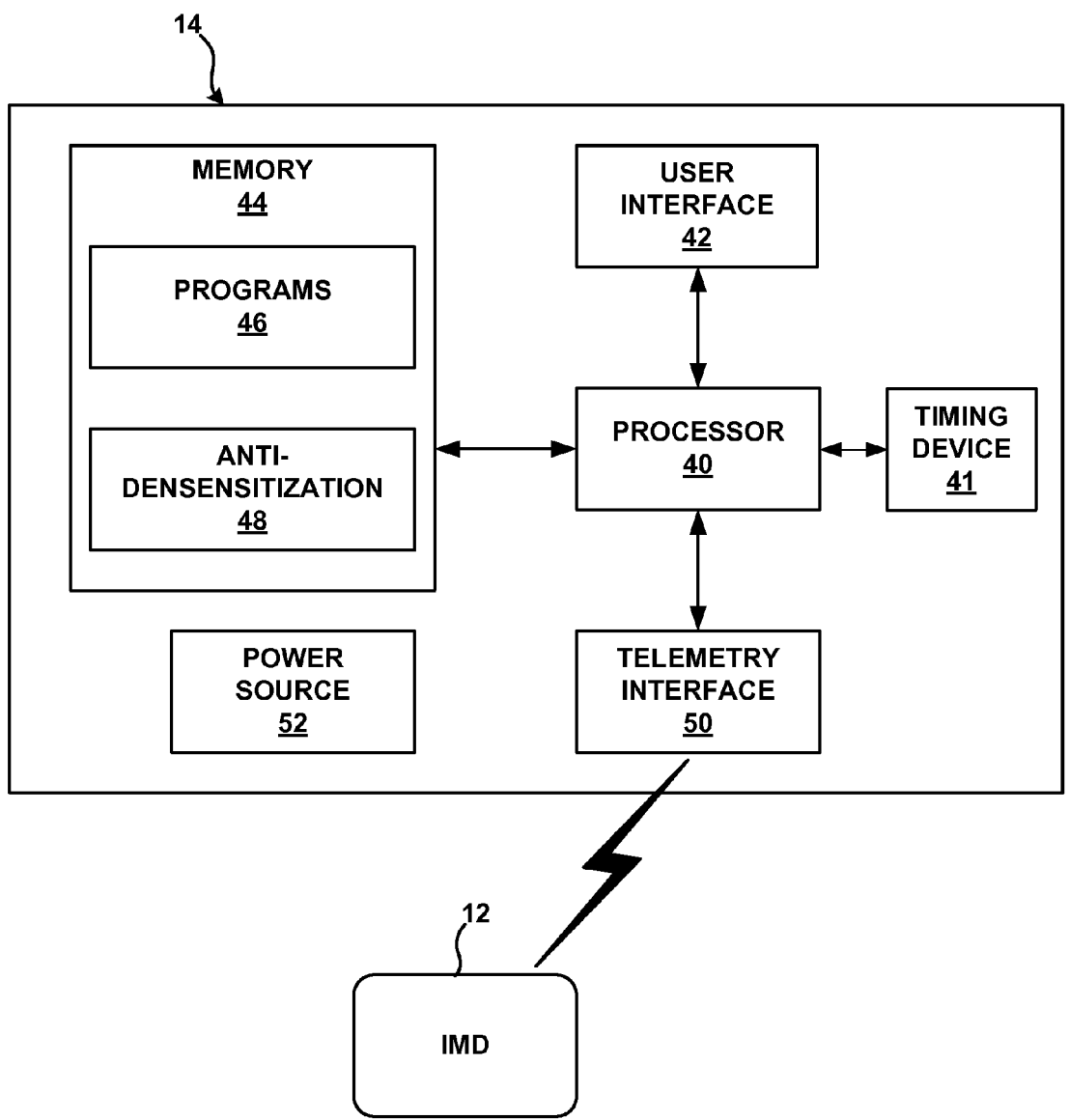
FIG. 3 is a block diagram illustrating example components of a patient programmer that receives patient input and communicates with a gastric electrical stimulator.

FIG. 3 is a block diagram illustrating example components of patient programmer 14 that receives patient input and communicates with stimulator 12. As shown in FIG. 3, patient programmer is an external programmer that patient 16 uses to control the gastric stimulation therapy delivered by stimulator 12. Patient programmer 14 includes processor 40, user interface 42, memory 44, telemetry interface 50 and power source 52. In addition, processor 40 may access a clock or other timing device 41 to adhere to lockout periods, therapy windows, and therapy schedules, as applicable. Patient 16 may carry patient programmer 14 throughout therapy so that the patient can initiate, stop and/or adjust stimulation as needed.

While patient programmer 14 may be any type of computing device, the patient programmer may preferably be a hand-held device with a display and input mechanism associated with user interface 42 to allow interaction between patient 16 and patient programmer 14. Patient programmer 14 may be similar to a clinician programmer used by a clinician to program stimulator 12. The clinician programmer may differ from patient programmer by having additional features not offered to patient 16 for security, performance, or complexity reasons.

User interface 42 may include display and keypad (not shown), and may also include a touch screen or peripheral pointing devices. User interface 42 may be designed to receive an indication from patient 16 to deliver gastric stimulation therapy. The indication may be in the form of a patient input in the form of pressing a button representing the start of therapy or selecting an icon from a touch screen, for example. In alternative examples, user interface 42 may receive an audio cue from patient 16, e.g., the patient speaks to a microphone in order to perform functions such as beginning stimulation therapy. Patient programmer 14 acts as an intermediary for patient 16 to communicate with stimulator 12 for the duration of therapy.

User interface 42 may provide patient 16 with information pertaining, for example, to the status of an indication or a gastric stimulation function. Upon receiving the indication to start stimulation, user interface 42 may present a confirmation message to patient 16 that indicates stimulation has begun. The confirmation message may be a picture, icon, text message, sound, vibration, or other indication that communicates the therapy status to patient 16. User interface 42 also may provide the status of an anti-desensitization feature to patient 16. For example, user interface 42 may indicate that the lockout period is currently active, e.g., with a small lock symbol displayed on the screen, or that a therapy window is about to expire.

In addition, user interface 42 may present information relating to the therapy schedule or therapy windows. In some cases, user interface 42 may prompt the patient 16 to initiate stimulation when a permitted time period on the therapy schedule has arrived. Alternatively, user interface 42 may display a lockout message pop up window to patient 16 if the user interface receives an indication from patient 16 to deliver therapy during the lockout period. In any case, user interface 42 may notify patient 16 when request indicated by patient input has been completed or cannot be completed due to a restriction.

Processor 40 may include one or more processors such as a microprocessor, a controller, a DSP, an ASIC, an FPGA, discrete logic circuitry, or the like. Processor 40 may control information displayed on user interface 42 and perform certain functions when requested by patient 16 via input to the user interface. Processor 40 may retrieve data from and/or store data in memory 44 in order to perform the functions of patient programmer 14 described herein. For example, processor 40 may generate a selection of electrodes as an anti-desensitization feature based upon instructions stored in memory 44, and processor 40 may then store the selection in memory 44.

Memory 44 may include programs 46 that are stimulation programs used to define therapy delivered to patient 16. When a new program is requested by stimulator 12 or patient 16, one of programs 46 may be retrieved from memory 44 and transmitted to stimulator 12 in order adjust the gastric stimulation therapy. Alternatively, patient 16 may generate a new program during therapy and store it with programs 46. Memory 44 may store instructions relating to anti-desensitization features 48, which may include instructions relating to the lockout period, therapy window, therapy schedule, burst pattern parameter selection, a burst pattern variation, and/or multi-site features. For the lockout period, for example, such instructions may define the duration of the lockout period, when to start and stop the lockout period, or any other parameters that may define the lockout period. Memory 44 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

While patient programmer 14 is generally described as a hand-held computing device, the patient programmer may be a notebook computer, a cell phone, or a workstation, for example. In some embodiments, patient programmer 14 may comprise two or more separate devices that perform the functions ascribed to the patient programmer. For example, patient 16 may carry a key fob that is only used to start or stop stimulation therapy. The key fob may then be connected to a larger computing device having a screen via a wired or wireless connection when information between the two needs to be synchronized. Alternatively, patient programmer 14 may simply be small device having one button, e.g., a single "start" button, that only allows patient 16 to start stimulation therapy when the patient feels hungry or is about to eat.

Stimulator 12 may store and implement any of the anti-desensitization features, such as the lockout period, the therapy window, and the selection of electrodes. When patient 16 presses the single start button to start stimulation again, the stimulation delivery may be subject to the anti-desensitization features, such as the lockout period, therapy window, and/or therapy schedule. In addition, in applying stimulation, programmer 14 and/or stimulator 12 may apply other anti-desensitization features, such as the burst pattern parameter selection, multi-site, and/or burst pattern variation features. Hence, in some embodiments, programmer 14 may have only a single start button that is accessible to the patient to attempt to activate stimulation, subject to one or more applicable anti-desensitization features that may control when or how stimulation is applied.

Figure 4:
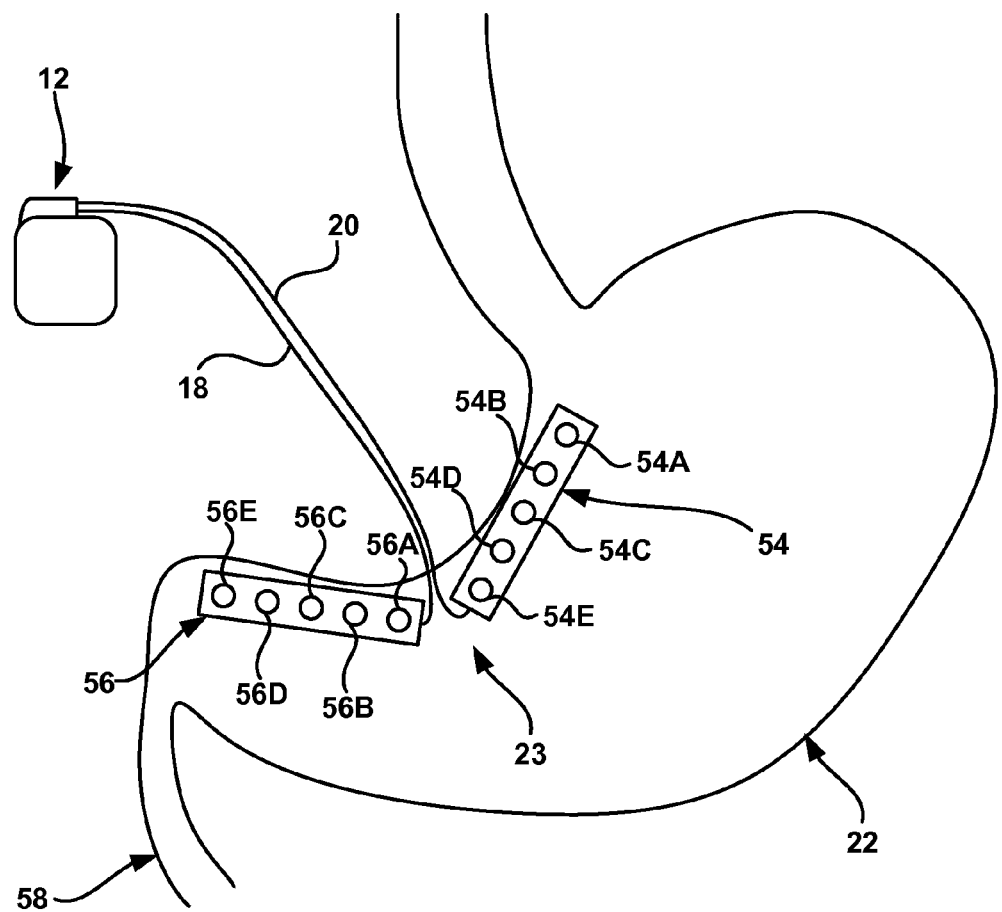
FIG. 4 is a conceptual diagram illustrating example electrode arrays positioned on the stomach of the patent for delivery of gastric electrical stimulation.

FIG. 4 is a conceptual diagram illustrating example electrode arrays 54 and 56 positioned on stomach 22 of patent 16. As shown in FIG. 4, electrode arrays 54 and 56 are attached to the outside of stomach 22. Electrode array 54 includes five discrete electrodes 54A, 54B, 54C, 54D and 54E (collectively "electrodes 54") and electrode array 56 includes five discrete electrodes 56A, 56B, 56C, 56D and 56E (collectively "electrodes 56"). Electrode arrays 54 and 56 are positioned along lesser curvature 23 of stomach 22, but the electrode arrays may be positioned anywhere upon stomach 22 as desired by the clinician. In addition, one or both electrode arrays 54 may be positioned at different sites, such as on the duodenum or elsewhere along the small intestine.

Electrode arrays 54 and 56 are provided in place of electrodes 24 and 26 of FIG. 1. In this manner, electrode arrays 54 and 56 may be used as part of a multi-site anti-desensitization feature to distribute electrical stimulation energy among a larger number of varied tissue sites, instead of concentrating stimulation at a single tissue site over an extended period of time. For example, electrode arrays 54, 56 may be used to support selection of different electrode combinations associated with different positions, or tissue sites, on a gastrointestinal organ such as the stomach. Each electrode array 54, 56 may include a plurality of electrodes, e.g., electrodes 54A-54E and electrodes 56A-56E, that may be individually selected to form a variety of electrode combinations that distribute electrical stimulation therapy to different therapy sites. Electrode combinations may include selected electrodes on different leads or the same lead. For example, an electrode combination may combine electrodes from array 54, array 56, or both array 54 and 56, as well as electrodes from other arrays, if provided. In general, electrodes in arrays 54, 54 may be positioned to form electrode combinations at tissue sites separated by greater than approximately 1 cm, greater than approximately 3 cm, or greater than approximately 5 cm. The distribution of stimulation among electrode combinations at different tissue sites may help to reduce desensitization and thereby extend the efficacy of electrical stimulation without compromising patient treatment.

In the example of FIG. 4, electrode arrays 54 and 56 and electrodes 54A-54E and 56A-56E may not necessarily be sized in proportion to stomach 22. For example, electrode arrays 54 and 56 may be configured to be a smaller size so that the electrodes can be packed into a smaller area of stomach 22. Alternatively, electrode arrays 54 and 56 and their corresponding electrodes may differ in size on stomach 22. For example, electrodes in array 54 may each have a larger surface area than each of the electrodes in array 56. In addition, electrodes 54 may have differing surface areas between each of the electrodes. In this manner, varying electrode surface area may act as an additional anti-desensitization feature to slightly alter the stimulation therapy over time.

Stimulator 12 may deliver electrical stimulation to stomach 22 using one or more electrodes of electrode arrays 54 and 56. Each of the electrodes in arrays 54, 56 may be coupled to stimulator 12 via a respective electrical conductor within leads 18, 20, and may be individually selectable. Each lead 18, 20 may include multiple conductors, each of which is coupled at a distal end to one of the electrodes in a respective electrode array 54, 56 and at the proximal end to a terminal of a switch device by which stimulator 12 directs stimulation energy to selected electrodes, e.g., as anodes or cathodes. In some examples, as mentioned above, stimulator 12 may deliver stimulation using one electrode from each of electrode arrays 54 and 56, multiple electrodes from one array and a single electrode from another array, or multiple electrodes in a single array.

Stimulator 12 may cycle through or randomly select different electrodes from each of electrode arrays 54 and 56 to produce different electrode combinations to vary the stimulation tissue sites throughout therapy. In other examples, stimulator 12 may deliver stimulation using a combination of any electrodes from only electrode array 54, only electrode array 56, or a combination of electrodes from electrode arrays 54 and 56. In alternative examples, the housing of stimulator 12 may also be used as an electrode. The housing of stimulator 12 may be referred to as a can electrode, return electrode, or active can electrode, as mentioned above.

While electrode arrays 54 and 56 are shown as each having five electrodes, electrode arrays 54 and 56 may have any number of electrodes desired by the clinician or necessary for efficacious therapy. Electrode arrays 54 and 56 may have differing numbers of electrodes, and stimulator 12 may be connected to a different number of electrode arrays, such as only one array or more than three arrays. In addition, electrode arrays 54 and 56 may have corresponding electrodes configured in a different orientation than the linear orientation shown in FIG. 4. For example, electrode arrays 54 and 56 may have electrodes oriented in a circular pattern, rectangular grid pattern, curved pattern, star pattern, or another pattern that may enhance the anti-desensitization feature of electrode arrays 54 and 56.

At some time during therapy, it is possible that one or more of electrodes 54 and 56 may no longer be functional due to a broken lead, broken conductor, disconnected circuit, corroded electrode, or some other problem. Stimulator 12 may recognize a dysfunctional electrode during an electrode integrity check at various times during therapy. Once an electrode is determined to be dysfunctional, stimulator 12 may remove that electrode from the possible electrodes for therapy. Stimulator 12 may also alter the algorithm used for generating a selection of electrodes for delivering therapy to ensure that only functional electrodes are included in the selection. In some examples, the clinician may manually alter the selection of electrodes when an electrode is determined to be dysfunctional.

In general, multiple electrodes implanted at multiple tissue sites, as shown in FIG. 4, may permit stimulation to be delivered to different stimulation sites at different times. For example, stimulation having substantially similar parameters or different parameters may be applied to different tissue sites during different therapy windows or therapy schedule time periods such that different tissue sites are stimulated to prevent or delay desensitization. The stimulation parameters may be selected to achieve similar therapeutic effects, e.g., gastric distention, even though the stimulating is delivered to different tissue sites.

Also, in some embodiments, stimulation may be delivered to different stimulation sites during the same therapy schedule periods or therapy windows. For example, therapy can be adjusted during the course of stimulation to use different electrode combinations and associated tissue sites. In addition, in other embodiments, a multi-site feature may be applied such that stimulation is delivered simultaneously or on an alternating, time-interleaved basis, e.g., pulse by pulse or burst by burst or burst pattern by burst pattern, to different electrode combinations and different associated tissue sites.

With reference to FIG. 4, for example, one pulse or burst could be applied to an electrode combination via array 54 while the next pulse or burst or burst pattern could be applied to an electrode combination via array 56. In this manner, a single tissue site is stimulated less often. Yet, the stimulation delivered to different tissue sites on an alternating basis may still achieve a substantially identical desired overall therapeutic effect, e.g., gastric distention, nausea or discomfort in the case of obesity.

Stimulator 12 may deliver first electrical stimulation therapy via a first electrode combination associated with a first position on the gastrointestinal organ for a first period of time, and deliver second electrical stimulation therapy to the gastrointestinal organ via a second electrode combination associated with a second position on the gastrointestinal organ for a second period of time. The stimulation therapies may comprises pulses, pulse trains, pulse bursts, burst patterns, or other patterns, and may include various duty cycles. Accordingly, the first and second period of time may generally refer to a period of time during which stimulation is actively delivered via a given electrode combination, even though stimulation may be delivered in different forms. Again, the first and second electrical stimulation therapies are configured to produce a substantially identical therapeutic result. In some cases, the first and second periods of time may be the same or different, and may partially overlap or not overlap with one another. If the first and second periods of time do not overlap, they may be separated by a gap in time or be arranged such that the second period of time commences immediately upon termination of the first period of time. In addition, the first and second periods of time may be greater than or equal to thirty seconds, greater than or equal to one minute, greater than or equal to five minutes, greater than or equal to ten minutes, greater than or equal to one hour, or greater than or equal to one day.

Again, delivery of the first and second gastric electrical stimulation therapy may be time-interleaved or time-independent. For example, different pulses or bursts of pulses or burst patterns may be delivered via electrode combinations at different positions on a time-alternating basis within a given therapy period or therapy window. Alternatively, different therapy periods or therapy windows may use different electrode combinations at different positions on a time-independent basis. In this latter case, instead of alternating between different positions, delivery of stimulation is generally time-independent in that stimulation may be delivered at a single given position for substantially an entire therapy period or window. Then, in a subsequent therapy period or window, stimulation may be delivered at a different, single given position for substantially the entire subsequent therapy period or window. In this case, delivery of stimulation is time-independent in the sense that there is no alternating of therapy at different positions within a given therapy period or window.

In summary, different electrode sets implanted at different locations on an applicable gastrointestinal organ, such as the stomach, may be used in different therapy periods, e.g., hours, or days, at different times within a given therapy period, or on alternating multi-channel, multi-site basis. Also, electrodes in one array 54 may be used for an extended period of time such as several seconds, minutes, hours, days or weeks, followed by transition to electrodes on the other array 56 after the extended period of time. In some cases, delivery of stimulation to one electrode set may at least partially overlap with delivery of stimulation to the other set of electrodes. However, at least portions of the stimulation delivered to the first and second electrode sets may not overlap. In other words, the first period of time for which stimulation is delivered to the first electrode set may either partially overlap or not overlap with the first period of time for which stimulation is delivered to the second electrode set. In each case, the stimulation delivered via the various electrodes is configured to support substantially the same therapeutic effect, such as gastric distension. Yet, the first and second electrode sets are displaced from one another by a sufficient distance so that different tissue sites receive the stimulation. As examples, electrodes in array 54 may be displaced from electrodes in array 56 by at least approximately 1 cm, more preferably at least approximately 3 cm, and still more preferably at least approximately 5 cm.

Figure 5A:
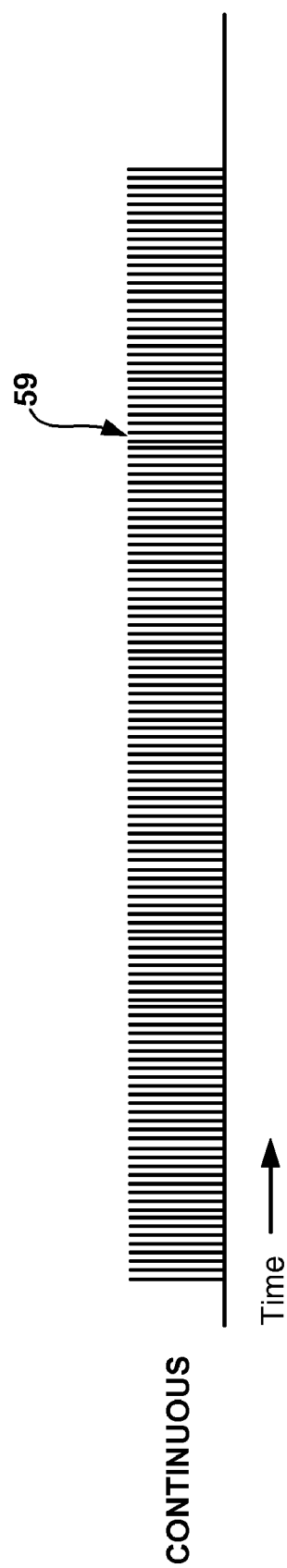
Figure 5B:
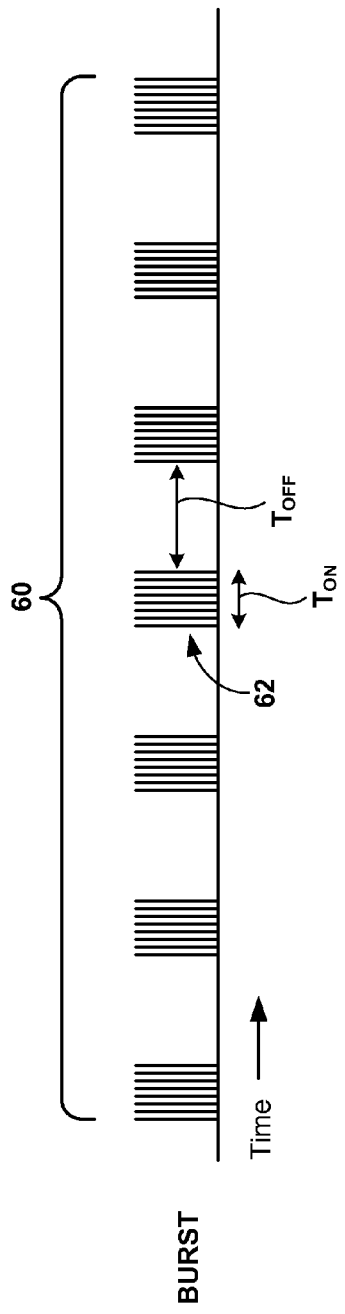
Figure 5C:
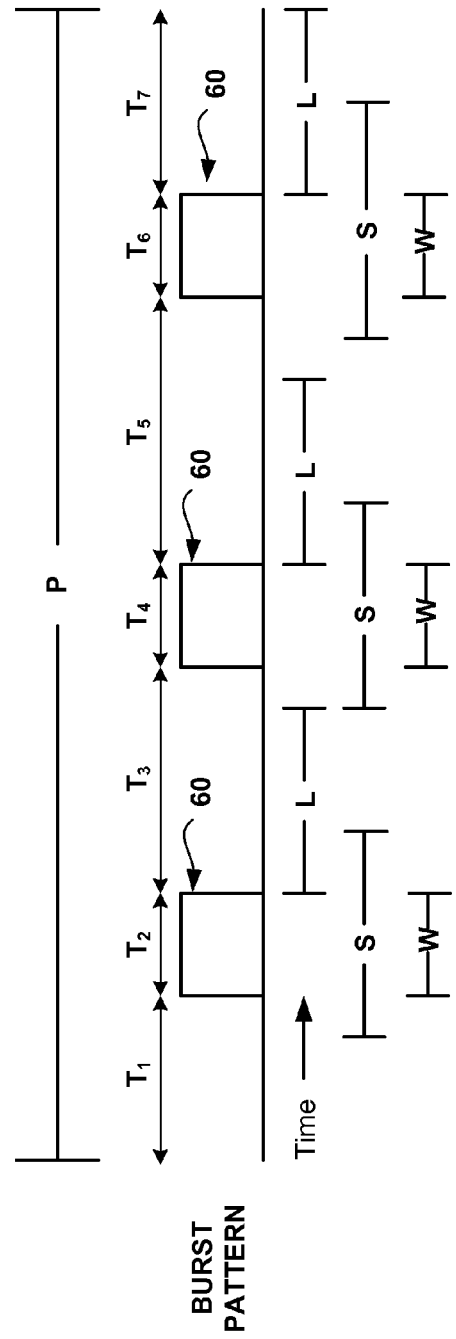

FIG. 5A is an example timing diagram illustrating a continuous train 59 of pulses that may be used in electrical stimulation delivered to patient 12. FIGS. 5B, 5C and 5D are example timing diagrams illustrating bursts of pulses that may be delivered as burst patterns in the electrical stimulation delivered to patient 16. As shown in FIG. 5B, electrical pulses generated by stimulator 12 may be delivered to patient 16 in bursts of pulses, where each pulse includes n pulses, and n is greater than one. The pattern of bursts may be a regular pattern or an irregular pattern. In addition, as shown in FIG. 5B, a burst pattern comprises multiple pulse bursts. FIG. 5C illustrates delivery of single burst patterns that generally conform to therapy windows. FIG. 5D illustrates delivery of multiple burst patterns within given therapy windows.

Each burst 62 includes multiple electrical pulses. In the example of FIG. 5B, $T_{on}$ is the time that stimulator 12 delivers continuous pulses that make up each burst 62, while $T_{off}$ is the time stimulator 12 is not delivering pulses between each burst 62. The ratio of $T_{on}$ to $T_{off}$ is the duty cycle of burst pattern 60 that is set by the clinician to provide effective therapy. The duty cycle of burst pattern 60 may be set anywhere between 0% and 100% ON. However, generally the duty cycle may be less than 50% ON and more than 50% OFF. Hence, a continuous train of pulses can be gated ON to form a pulse burst. Likewise, a series of pulse bursts may be gated ON to form a burst pattern 60 containing multiple pulse bursts 62. Stimulation may be delivered, in various embodiments, as pulses, bursts, burst patterns, continuous pulse trains, or the like.

While FIG. 5B illustrates each burst 62 having eight pulses and burst pattern 60 having seven bursts for purposes of illustration, any number of pulses and bursts 62 may define one burst pattern 60. For example, burst pattern 60 may include over one hundred bursts while each burst 62 may include more than 20 pulses. Alternatively, burst pattern 60 may include fewer bursts 62 with each burst having fewer pulses. A clinician may program stimulator 12 to deliver burst pattern 60 to patient 16 with the desired number of bursts 62 and pulses to treat patient 16. The pulses of bursts 62 and each of the bursts may be delivered according to example stimulation parameters described herein.

FIG. 5C illustrates an example therapy schedule time period P that includes multiple therapy applications within therapy windows W. Hence, one or more therapy windows W may be applied during a therapy schedule time period P. For example, period P may be equal to a 24 hour day of patient 16, e.g., from midnight to midnight. In the examples of FIGS. 5C and 5D, the lockout period L prevents stimulator 12 from delivering stimulation within a predetermined period of time following termination of stimulation. In this manner, lockout period L, whether maintained by stimulator 12 or patient programmer 14, functions as an anti-desensitization feature by preventing continuous or excessive delivery of stimulation. Instead, stimulation is generally delivered when needed, rather than at times when the stimulation is not necessary, such as between meals or while the patient is sleeping. In addition, stimulator 12 and/or patient programmer 14 may implement additional anti-desensitization features in the form of therapy windows and a therapy schedule.

As shown in FIGS. 5C and 5D, delivery of therapy may be permitted only during schedule times S permitted by a therapy schedule. Times S may be substantially coincident with meal times and, optionally, snack times. Each time S may extend over a period of time in which it is likely that the patient may ingest a meal. For breakfast, for example, the time S may run from 6 am to 8 am. As mentioned previously, times S on the therapy schedule may have start and/or end times and/or durations that vary from day to day, as another anti-desensitization feature. If therapy is requested during a schedule time S, then therapy may be delivered, e.g., by transmission of a command from patient programmer 14 to stimulator 12, subject to other anti-desensitization features. If therapy is requested outside of one of the schedule times S, however, than delivery of therapy is not permitted, either by refusal of programmer 14 to transmit a request or refusal of stimulator 12 to deliver stimulation in response to a request from the programmer.

With further reference to FIG. 5C, a therapy window W specifies a maximum time for which therapy may be delivered. In this manner, the therapy window W limits the duration for which stimulation is delivered at a given time. As mentioned previously, the therapy window W may selected based on a first period of time that is found to be sufficient to cause a desired physiological response or therapeutic result for a second period of time. The second period of time may be greater than or less than the first period of time, but extends at least in part beyond the end of the first period of time. The first period of time may be selected to produce the desired therapeutic effect for the second period of time and, in some cases, may be the minimum period of time sufficient to produce the desired therapeutic effect for the second period of time.

In the case of gastric distention, for example, the desired therapeutic effect, response or result may be a maintenance of an increase in gastric volume at a threshold percentage of a target level, e.g., a 50% volume increase above a baseline level of gastric volume. Programmer 14 and/or stimulator 12 may start a clock or other timing device upon initiation of delivery of therapy and then require termination of therapy prior to expiration of an applicable therapy window W, which corresponds to the first period of time sufficient to produce the desired therapeutic effect for the second period of time. In this manner, any single administration of therapy is limited in time by the therapy window W in order to reduce the likelihood of desensitization, and possibly conserve power resources. As described above, the therapy window W may be selected to be the approximately the minimum time necessary to achieve a desired therapeutic effect for a desired period of time, i.e., the second period of time, given a set of stimulation parameters and/or other factors.

Alternatively, the therapy window W may be approximately this minimum time plus an optional margin such that the therapy window W is somewhat greater than or equal to the minimum. In any event, the therapy window is a function of an approximate duration of the gastric electrical stimulation therapy that is effective in producing a desired therapeutic effect for a desired period of time during and after termination of the gastric electrical stimulation therapy. Notably, the therapy window may be shorter than the desired period of time for which the therapeutic result is produced because the recovery time of the tissue may permit the therapeutic result to be prolonged to a desired degree for an extended period of time following termination of delivery of stimulation.

The length of the therapy window W, like the lockout period L and scheduled time S may be the same throughout the day, or may vary for different meals. For example, a patient 16 may desire a longer schedule time S for dinner, to permit flexible dinner planning. Also, the therapy window W may be increased for some meals, such as dinner, which may have a more leisurely pace to provide an extended period in which the desired therapeutic effect is available. If therapy starts within a schedule time S, the therapy may be permitted to extend beyond the schedule time S, subject to the maximum time specified by the therapy window W. Alternatively, therapy may be terminated at the end of the scheduled time S if it would extend beyond the scheduled time S.

In some embodiments, each therapy application within a therapy window W may contain one or more burst patterns 60 containing multiple bursts 62. A single burst pattern 60 may reside within each therapy window W and form the therapy application for a particular therapy schedule time period S. Alternatively, a therapy window W may include multiple burst patterns 60, e.g., as shown in FIG. 5D. Each time that therapy is delivered to patient 16, stimulator 12 delivers bursts of pulses as described above for burst pattern 60.

The beginning of each therapy application in a therapy window W may be related to when patient 16 eats a meal, and may be either initiated by patient 16 or scheduled by stimulator 12. When initiated by a patient, delivery of the therapy is permitted within a permitted time S, per the therapy schedule. The therapy may be initiated at any time within the time S, and need not be at the beginning of the time S. Once started, however, the therapy generally is limited to the duration of an applicable therapy window W, e.g., to avoid or reduce desensitization and/or conserve power.

As shown in FIG. 5C, stimulator 12 delivers therapy to patient 16 during times $T_2$, $T_4$ and $T_6$. During times $T_1$, $T_3$, $T_5$, and $T_7$, no electrical stimulation is delivered to patient 16. At the end of each therapy application, which is coincident with a therapy window W, system 10 implements lockout period L to prevent stimulator 12 from delivering therapy to patient 16 until lockout period L has elapsed, either by directly locking out stimulator 12 from delivery therapy or locking out patient programmer 14 from transmitting a command to initiate delivery of therapy during the lockout period. In addition, after the end of each therapy window W, a desired therapeutic effect may remain in effect for some time.

Therapy windows W and burst patterns 60 may be substantially equivalent with one another throughout period P or different. Likewise, lockout periods L may be substantially equivalent throughout period P or different. As an alternative, in some cases, therapy windows W and burst patterns 60 may change in timing and/or duration. For example, timing and/or duration of burst patterns 60 may change depending upon the time of day the therapy is started. If multiple burst patterns, each containing multiple pulse bursts, are delivered within an applicable therapy window, the timing between successive burst patterns may be fixed or variable. If the timing is variable, the time between burst patterns may be the same throughout a given burst pattern. Alternatively, the times between different burst patterns in a given window W may vary. In addition, the duration of burst patterns delivered to the patient may vary among different therapy windows, or within a given therapy window. Also, the durations of burst patterns may vary among different therapy windows, or within a given therapy window.

As an illustration, for purposes of example and without limitation, a particular therapy window could include x burst patterns. Each burst pattern could include y pulse bursts. Each pulse burst could include z pulses. Each burst pattern could have a duration of time $t_1$, and be separated in time by time $t_2$. In operation, the number x of burst patterns could be varied from therapy window to therapy window. The number of bursts y and pulses in each burst z could likewise be varied. In addition, the times $t_1$ and $t_2$ could be varied from therapy window to therapy window or within a given therapy window such that some burst patterns in a window have different durations, and such that the time between successive burst patterns in a window is different.

FIG. 5D shows multiple burst patterns provided in successive therapy windows. For example, four burst patterns 60A of equal duration and equal time spacing between successive burst patterns are provided in a first therapy window W at time $T_2$. Three burst patterns 60B of different durations and different time spacing are provided in the next therapy window W at time $T_4$. Four burst patterns 60C of equal duration but different time spacing are provided in the therapy window W at time $T_6$. Hence, multiple types of variation may be introduced into the burst patterns to provide further variation that may prevent or delay desensitization of stimulated tissue in patient 16.

With further reference to FIGS. 5C and 5D, lockout period L may also be vary, e.g., as a function of the time of day. For example, lockout periods L may be shorter in duration during the morning while lockout periods L in the evening may be longer to prevent patient 16 from sleeping with undigested food in stomach 22. In addition, times between successive therapy applications may vary due to when patient 16 eats. As shown in FIG. 5C, time $T_5$ is greater than times $T_1$, $T_3$ and $T_7$.

In other examples, period P may include more or less than three burst applications, as needed by patient 16 and allowed by the clinician.

FIG. 5E shows delivery of various burst patterns throughout a period P. Whether lockout periods L, schedule times S, and therapy windows W are used or not, FIG. 5E illustrates delivery of stimulation using burst patterns that may vary in number, duration and/or timing from period to period P. In a first period P, for example, burst patterns may be delivered as indicated by 60D, 60F and 60H. In a second period P, burst patterns may be delivered as indicated by 60E, 60G, 60I, and 60J. As shown in FIG. 5D, the burst patterns may be delivered with different start times and durations. In addition, the number of burst patterns may vary from period to period, e.g., as shown by burst pattern 60J.

Although a relatively small number of burst patterns are shown in FIG. 5E, a much larger number of burst patterns may be delivered. As one example, programmer 14 and/or stimulator 12 may be configured to deliver burst patterns having durations of 1 to 60 minutes, with a number of burst patterns per 24-hour period being variable from 1 to 100 burst patterns. By varying the timing, duration and number of burst patterns from period to period, desensitization can be prevented or delayed. In addition, desensitization can be prevented or delayed by delivering multiple burst patterns at different times and with different durations within a given period. In some embodiments, the number, timing and duration of burst patterns may be specified by a clinician or permitted to vary automatically, e.g., randomly, within limits specified by the clinician via a physician programmer, according to a randomization algorithm or other algorithm used by programmer 14 and/or stimulator 12.

Figure 5F:
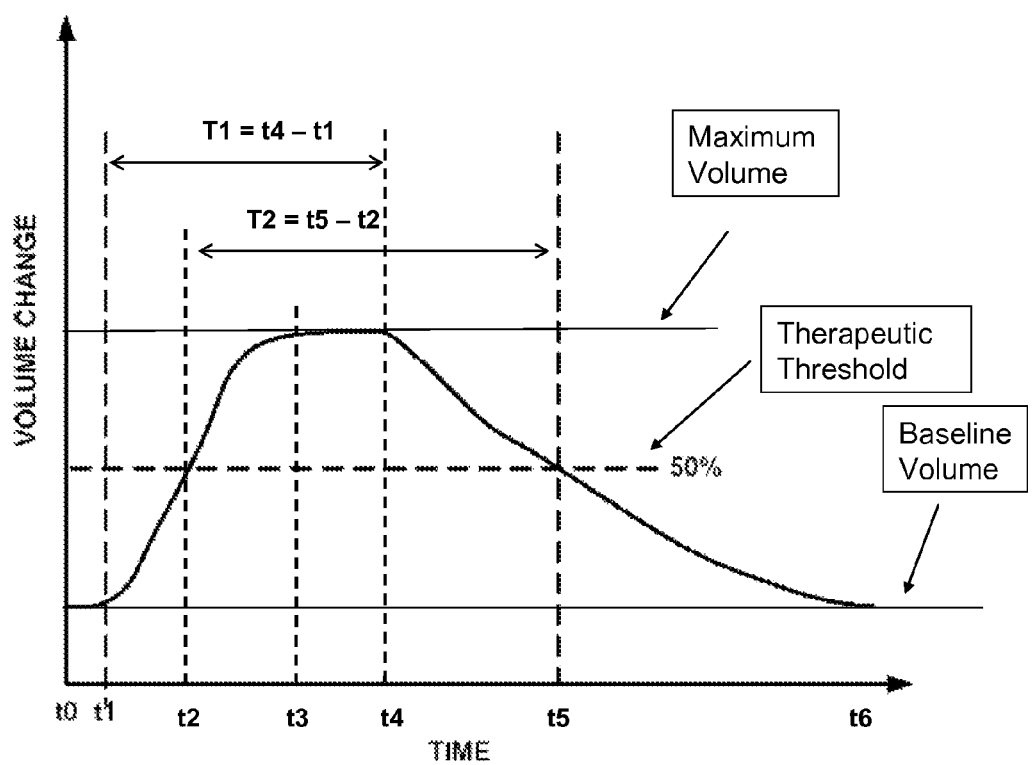
FIG. 5F is a graph illustrating gastric distention during and following application of stimulation within a therapy window.

FIG. 5F is a graph illustrating gastric distention during and following application of stimulation within a therapy window. The graph of FIG. 5F is provided for purposes of illustration and depicts the concept of a therapy window and associated gastric distention response. Accordingly, FIG. 5F does not represent actual data and is not drawn to scale. In the example of FIG. 5, stimulation is delivered for a first period of time T1=t4−t1, consistent with a therapy window. In particular, following an initial time t0, stimulation is delivered at time t1 and maintained until time t4 During stimulation, gastric volume increases, and reaches a therapeutic threshold (defined here as a gastric volume that is 50% greater than gastric volume at baseline t0) at time t2, and at a later time t3, reaches a maximum level.

Delivery of stimulation may continue until time t4. When stimulation is terminated at time t4, gastric volume gradually decreases, reaching the threshold for therapeutic efficacy (the therapeutic threshold) at time t5. By time t6, gastric volume has decayed back to baseline levels obtained at t0. Thus, by applying stimulation for a time T1, gastric volume is increased over baseline levels to a therapeutic range for a time T2. As the time for increasing gastric volume after the onset of stimulation is generally greater than the time for gastric volume to return to baseline levels after termination of stimulation, T2 will generally be greater than T1.

Note that, in this discussion, gastric volume is used as an example of a measure of muscle tone. Other terminology may also be used interchangeably including gastric distention, gastric tone, gastric volume, gastric relaxation. Other measures of gastric relaxation may include changes in length of any segment of the stomach, or the thickness of the stomach muscle wall, as measured by ultrasound, magnetic, mechanical, optical, or other electronic transducers;

In the example of FIG. 5F, the gastric stimulation produces an increase in gastric volume relative to an initial volume prior to stimulation. After stimulation is stopped at time t4, the gastric volume does not immediately return to the initial volume. Rather, gastric volume decays somewhat slowly such that gastric volume remains above the target threshold level (i.e., a volume that is 50%≧baseline volume) achieved by stimulation until time t5. If the desired therapeutic effect occurs when gastric volume remains above the target threshold level (i.e., gastric volume remains≧50% above baseline gastric volume), then the desired therapeutic effect persists for an additional time t5−t4 following cessation of stimulation. Hence, stimulation for a first period of time T1=t3−t1 can produce a desired therapeutic effect for a second period of time T2=t5−t2, wherein T2 is greater than T1.

Figure 6A:
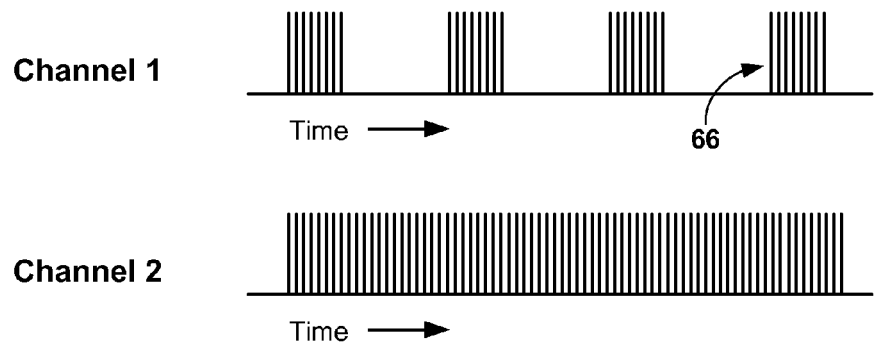
FIGS. 6A, 6B and 6C are example timing diagrams illustrating continuous pulses and bursts of pulses delivered to the patient via two different channels.
Figure 6B:
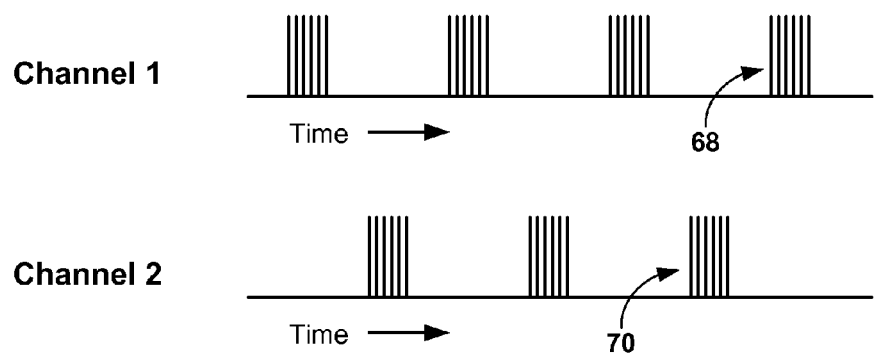
Figure 6C:
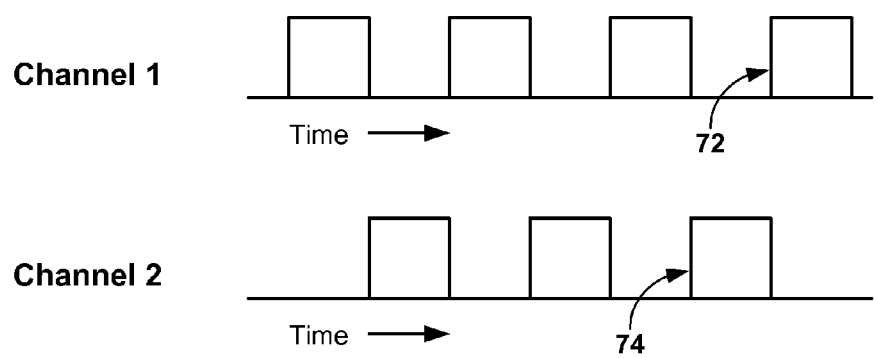

FIGS. 6A, 6B and 6C are example timing diagrams illustrating continuous pulses and bursts of pulses delivered to patient 16 when system 10 delivers therapy to multiple distinct sites, i.e., via multiple, different physical channels, as part of a multi-site anti-desensitization feature. Such channels may be realized by different electrodes and associated conductors within leads 18, 20 that can be selected to deliver therapy. Channels 1 and 2 will be described herein as example channels that deliver stimulation therapy. Channels 1 and 2 may both indicate stimulation delivered to the same organ such as stomach 22 or the small intestine via respective electrode combinations. The small intestine may be stimulated, e.g., at the duodenum or the jejunum, for example. The stomach may be stimulated, e.g., in the lesser or greater curvature.

FIG. 6A illustrates a timing diagram for two channels, channel 1 and channel 2. Channels 1 and 2 deliver stimulation to a different electrode combinations. In the example of FIG. 6A, channel 1 delivers bursts 66 of discrete pulses over time while channel 2 delivers a continuous train of pulses. Pulses delivered by channel 1 and channel 2 may have the same parameters or different parameters, depending upon the tissue treated by channels 1 and 2, and may be delivered together within the same therapy window. However, the stimulation delivered via channel 1 and channel 2 is selected to produce substantially the same therapeutic effect.

FIG. 6B shows bursts 68 of pulses on channel 1 and bursts 70 of pulses on channel 2 for multi-site gastric stimulation. Pulse bursts 68 and 70 are shown in synchronous burst mode such that bursts 68 and 70 have equivalent duty cycles. Bursts 68 and 70 are offset from each other in time, such that they are delivered on an alternating basis, but the bursts may also be delivered at the same time in some example embodiments. Bursts 68 and 70 are delivered during the ON portion of the duty cycle. Pulse bursts 68 and 70 may be delivered in a variety of different modes, such as a continuous mode, an asynchronous burst mode, or a synchronous burst mode. In a continuous mode, the pulse train is delivered relatively continuously over an active period in which stimulation is "ON." In an asynchronous burst mode, the pulse train is delivered in periodic bursts during the active period. The continuous and asynchronous burst modes do not rely on synchronization between channels 1 and 2.

In a synchronous burst mode, the pulse train is delivered in bursts that are synchronized with multiple channels, such as channels 1 and 2. In this sense, the synchronous burst mode may be viewed as a closed loop approach. Stimulator 12 may synchronize electrical stimulation between channels 1 and 2 in order for the resulting organ response to stimulation to be matched for maximal efficacy. Channels 1 and 2 may activate stimulation to cause gastric distention and thereby discourage the intake of excessive amounts of food. In the example of FIG. 6B, the alternating bursts may be delivered on a time-interleaved basis within the same therapy window. The duration of each burst may be greater than or equal to approximately thirty seconds. By shifting between different electrode combinations on a time-interleaved basis, a multi-site stimulation feature may reduce tissue desensitization.

FIG. 6C illustrates alternating burst patterns 72 and 74 between different electrode combinations on channels 1 and 2. Each of burst patterns 72 and 74 includes multiple bursts of electrical pulses, e.g., like bursts 68 or 70 of FIG. 6B. The alternating burst patterns 72, 74 may be delivered on a time-interleaved basis within the same therapy window. Burst patterns 72 and 74 may be referred to as alternating synchronous burst patterns because stimulator 12 only delivers one of burst patterns 72 and 74 at any given time. In some examples, bursts 72 and 74 may be provided such that the burst patterns on channels 1 and 2 overlap or are separated by a certain interval. The duration of each burst pattern may be greater than or equal to approximately thirty seconds.

Hence, FIG. 6A shows channel 1 delivering pulse bursts and channel 2 delivering continuous pulses, FIG. 6B shows synchronous delivery of pulse bursts on an alternating basis between channel 1 and channel 2, and FIG. 6C shows synchronous delivery of burst patterns, each containing multiple pulse bursts, on an alternating basis between channel 1 and channel 2. In each case, stimulator 12 may use multi-cite stimulation on channel 1 and channel 2 as an anti-desensitization feature to prevent or delay sensitization of a tissue site. The pulses, bursts, or burst patterns may be delivered to different electrode combinations at different times to reduce desensitization.

With multi-site stimulation, stimulator 12 may deliver essentially the same type of stimulation to achieve essentially the same type of therapeutic effect via two or more different physical channels (i.e., two different electrode combinations) to two different stimulation sites with the same or similar stimulation parameters. As an example, stimulator 12 may deliver stimulation with similar parameters to two different tissue sites on an alternating basis. The parameters may be selected such that the stimulation of the different tissue sites, while preventing or delaying desensitization, produce a desired overall therapeutic effect, such as gastric distension or regulation of motility.

Stimulation parameters may be identical or differ slightly for electrodes stimulating different tissue sites. In either case, however, it is desirable that the parameters of stimulation delivered on channels 1 and 2 be selected to achieve substantially the same therapeutic effect. If gastric distention is desired, for example, then stimulation parameters on channels 1 and 2 may be selected to support gastric distention, and preferably similar amounts of gastric distention.

Although two channels are described for purposes of illustration, stimulator 12 may apply stimulation via three, four or more channels for multi-site stimulation to achieve similar therapeutic effects. For example, stimulator 12 may be coupled to multiple leads to deliver stimulation to different electrodes on the multiple leads. Alternatively, stimulator 12 may select multiple electrode combinations available using electrodes deployed on a single implantable lead.

Stimulator 12 also may distribute pulsed stimulation therapy to at least one of multiple tissue sites, e.g., via channels 1 and 2, in order to provide another anti-desensitization feature to patient 16. Delivery of pulse bursts or burst patterns to multiple stimulation sites on an alternating basis may be preferred so that none of the stimulation sites receives continuous stimulation. Instead of providing substantially continuous electrical pulses to stomach 22 via one channel, stimulator 12 may spread out the electrical stimulation to multiple tissue sites via channels 1 and 2, where each channel includes electrodes positioned at different tissue sites. The resulting therapy may be effective in causing gastric distention or other desired effects, but prevents or delays desensitization of the tissue that could otherwise result from delivering continuous pulses to the same tissue site on a persistent basis. Instead, the tissue site receives stimulation intermittently, according to any of the multi-channel pulse or burst approaches illustrated in FIGS. 6A-6C.

FIGS. 7A, 7B, 7C, 7D, and 7E are example timing diagrams illustrating relative timing of stimulation delivered via different channels in association with a multi-site stimulation feature. In the examples of FIGS. 7A-7E, first, second and third channels deliver first, second and third electrical stimulation therapy to a gastrointestinal organ via first, second and third electrode combinations, respectively. The first, second and third electrode combinations are associated with first, second and third positions on the gastrointestinal organs. The first, second and third stimulation therapy are delivered for first, second and third periods of time, respectively, where each period of time is greater than approximately thirty seconds, greater than or equal to one minute, greater than or equal to five minutes, greater than or equal to ten minutes, greater than or equal to one hour, or greater than or equal to one day. The first, second and third stimulation therapies are configured to produce a substantially identical therapeutic result, such as distention. The first, second, and third period of time may partially overlap or not overlap, and may be same or different durations.

Figure 7A:
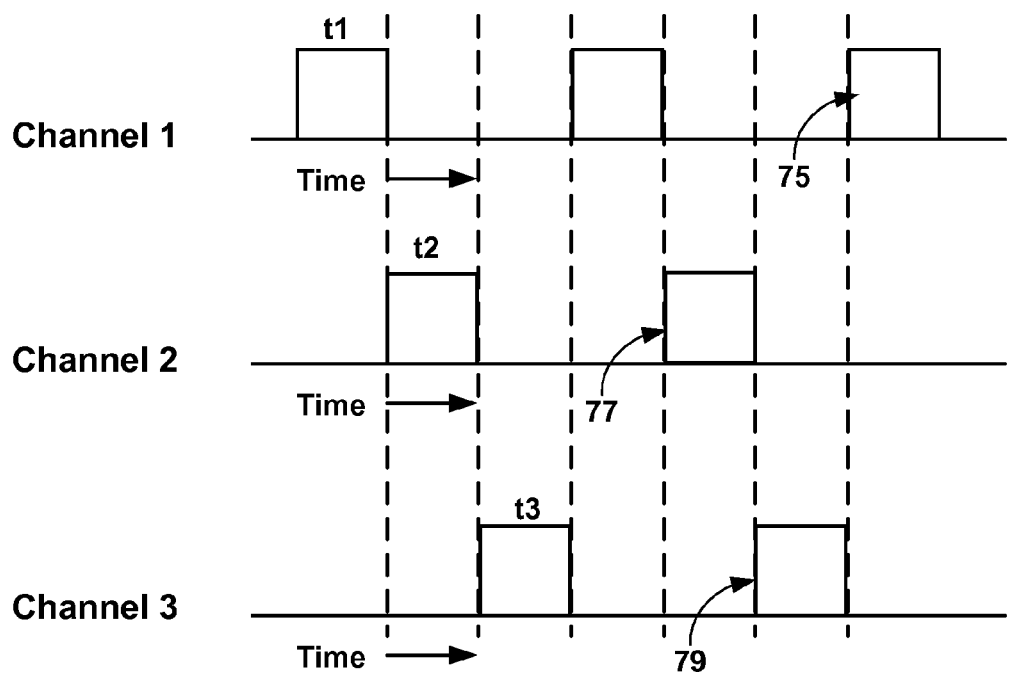
FIGS. 7A, 7B, 7C, 7D, and 7E are example timing diagrams illustrating relative timing of stimulation delivered via different channels.

As shown in FIG. 7A, first, second and third stimulation therapies 75, 77, 79 may be delivered on Channels 1, 2, and 3, respectively, to selected electrode combinations, e.g., as pulses, bursts, burst patterns, or continuous pulse trains. In the example of FIG. 7A, the stimulation 75, 77, 79 on each channel is ordered such that first stimulation 75 on Channel 1 is delivered for a first period of time t1, second stimulation 77 is then delivered for a second period of time t2 after the first stimulation is stopped, and third stimulation 79 is then delivered for a third period of time t3 after the second stimulation is stopped. In this example, the stimulations on Channels 1, 2 and 3 do not overlap. Instead, stimulation on one channel starts upon cessation of stimulation on another channel. However, overlapped stimulation may be used in other embodiments. Also, in FIG. 7A, stimulation one channel starts immediately upon cessation of stimulation on the previous channel. In other embodiments, however, a time gap may be provided between successive stimulations on different channels.

Figure 7B:
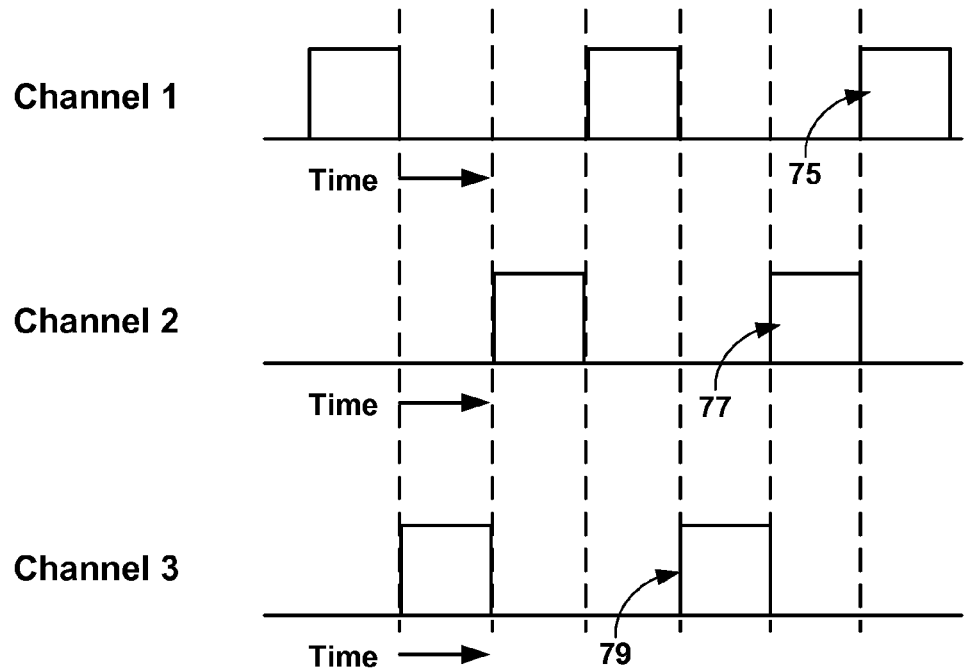

In FIG. 7A, stimulation is ordered such to apply first stimulation 75 on Channel 1, followed by second stimulation 77 on Channel 2, followed by third stimulation 79 on Channel 3. In the example of FIG. 7B, however, the order is changed to apply first stimulation 75 on Channel 1, followed by third stimulation 79 on Channel 3, followed by second stimulation on Channel 2. The order may be fixed or varying and may be selected by a physician. In some cases, a randomization or pseudo-randomization function may be applied to select the ordering of the Channels. In each case, the stimulation delivered on each channel may be greater than approximately thirty seconds.

The positioning of the electrode combinations associated with Channels 1, 2 and 3 may be unrelated to the ordering. For example, in some cases, the first, second and third positions may be arranged such that the first position is most proximal on the gastrointestinal organ, the third position is most distal on the gastrointestinal organ, and the second position is between the first and third positions, yet stimulation need not be applied along a particular axis relative to the gastrointestinal organ. In general, there are no restrictions on alignment or orientation of different electrodes with respect to the GI tract. In particular, the electrodes do not need to be positioned or aligned to produce a functional peristaltic activity. The stimulation ordering and positioning of the multiple electrode combinations may be flexible. Accordingly, the ordering need not be related to the positions of the electrode combinations on the gastrointestinal organ, particularly where stimulation is configured to produce distention, nausea or discomfort, and not to regulate motility by peristaltic function.

Figure 7C:
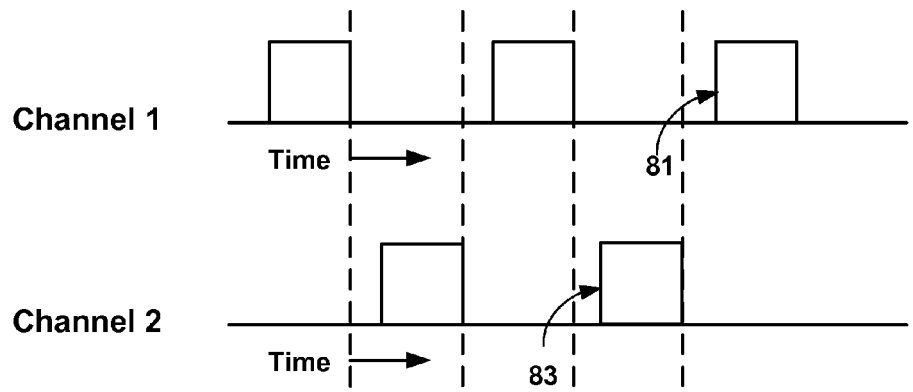

In the example of FIG. 7C, first and second stimulation 81, 83 are applied via Channel 1 and Channel 2, respectively, with a time delay between cessation of delivery of the first stimulation delivery and the start of delivery of the second stimulation, and vice versa. Hence, in contrast to the example of FIGS. 7A and 7B, the next stimulation does not commence immediately following the previous stimulation. Instead, there may be a delay between stimulation via different electrode combinations. The delay may be greater than approximately one second, ten seconds, thirty seconds, one minute, or longer.

Figure 7D:
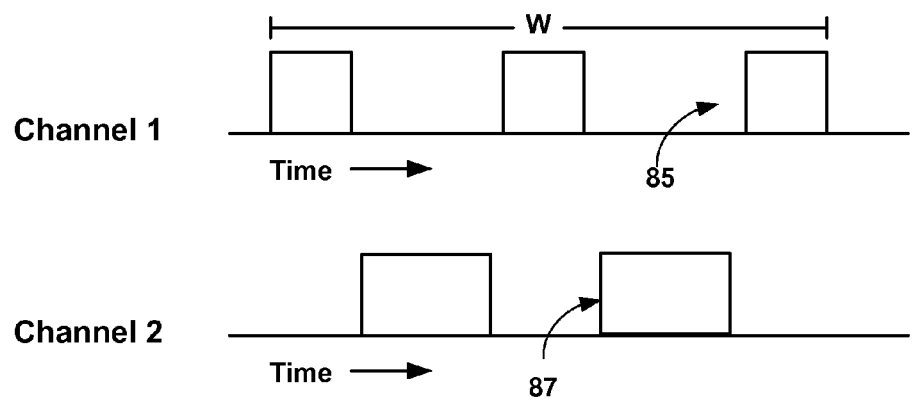
Figure 7E:
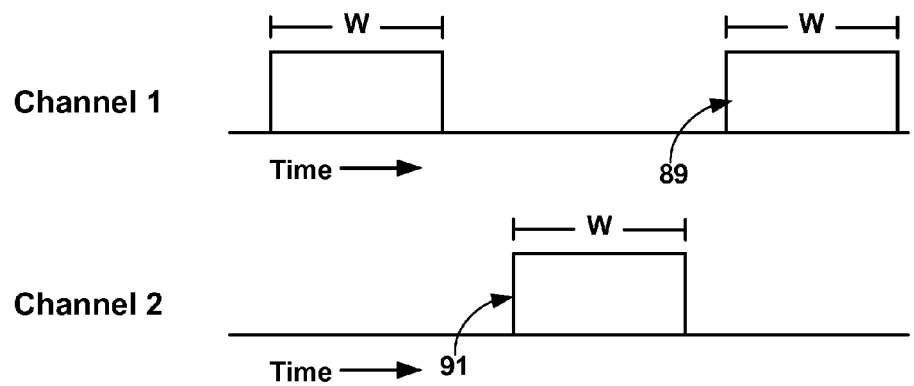

FIG. 7D shows the delivery of first and second stimulation 85, 87 via different electrode combinations associated with Channels 1 and 2 within the same therapy window W on a time-interleaved basis. In this case, stimulation delivered during a therapy window, as described herein, is provided by stimulation from two or more Channels, which are time-interleaved with one another within the therapy window. In the example of FIG. 7E, however, first and second stimulation 89, 91 are delivered via different electrode combinations associated with Channels 1 and 2 within different therapy windows W on a time-independent basis. For example, first stimulation may be delivered via a first electrode combination for a first period of time associated with an entire therapy window W, and then second stimulation may be delivered via a second electrode combination for a second period of time associated with an entire, different therapy window.

Again, the first and second stimulation therapies may comprise pulses, pulse trains, pulse bursts, burst patterns, or other patterns, and may include various duty cycles. The first and second periods of time may generally refer to a period of time during which stimulation is actively delivered via a given electrode combination, even though stimulation may be delivered in different forms. Accordingly, delivery of stimulation for a period of time does not necessarily require that stimulation pulses are delivered continuously during that time. Rather, it is sufficient that stimulation be actively delivered, subject to gaps or delays associated with pulses, bursts, burst patterns or other waveforms that may be specified for the stimulation, e.g., as stimulation parameters.

Figure 8A:
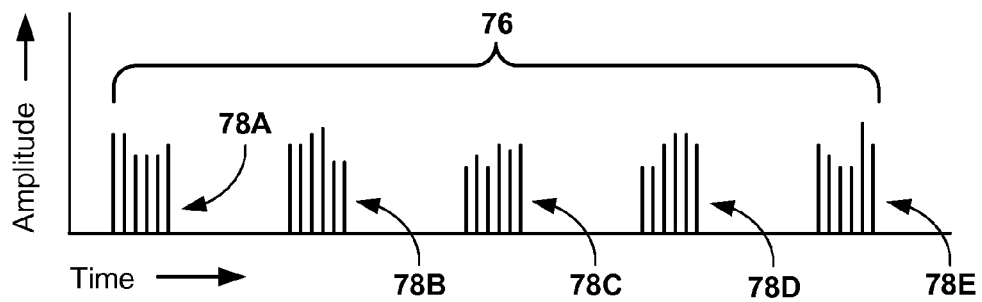
FIGS. 8A, 8B and 8C are example timing diagrams illustrating bursts of pulses having variations between bursts.
Figure 8B:
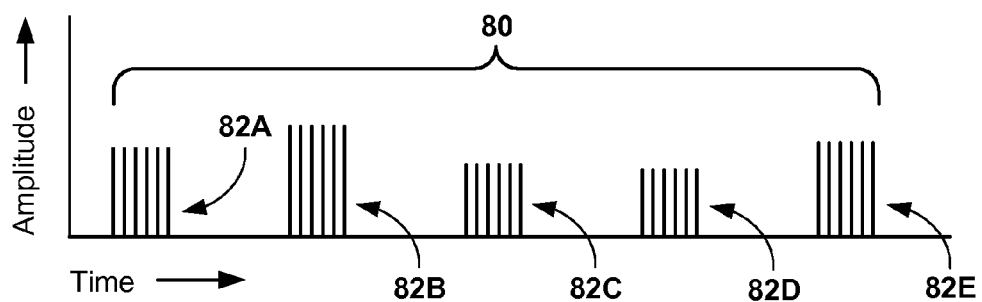
Figure 8C:
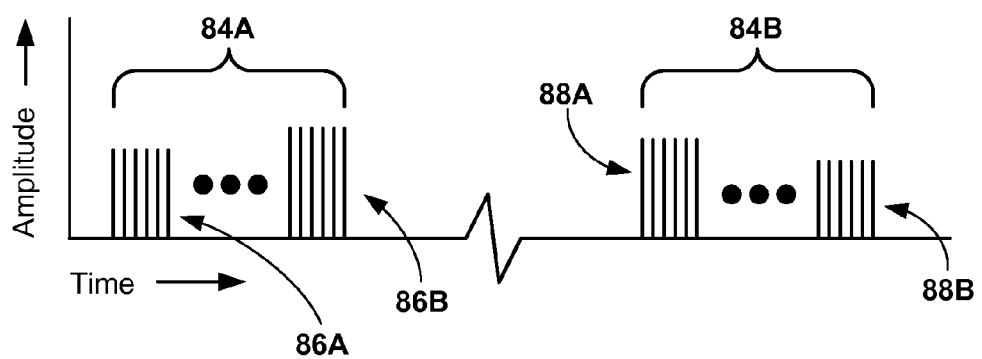

FIGS. 8A, 8B and 8C are example timing diagrams illustrating bursts of pulses having variations between the pulses of the bursts. As shown in FIG. 7A, burst pattern 76 includes multiple bursts 78A, 78B, 78C, 78D and 78E (collectively "bursts 78) of discrete pulses. Burst pattern 76 and bursts 78 may be similar to burst pattern 60 and bursts 62, respectively, as described in FIGS. 5A and 5B. Burst patterns as shown in FIGS. 8A-8C may be used in conjunction with other anti-desensitization features, such as multi-site stimulation, therapy windows, and lockout intervals. The pulses of each of bursts 78 may vary in voltage amplitude within each burst such that at least two pulses within each burst have different voltage amplitudes. In addition, each subsequent burst may contain a sequence of pulses that is not identical to the sequence of pulses of the previous burst. These variations in voltage amplitude of the pulses may help to prevent or delay desensitization. For example, the pulses of burst 78A are not identical to the pulses delivered during burst 78B. While voltage amplitude is the stimulation parameter described in FIGS. 8A, 8B and 8C, the pulses may vary by any stimulation parameter, such as current amplitude, pulse width, or pulse rate.

The pulses of bursts 78 vary within each burst randomly within a predetermined range. The resulting pulses may have any voltage amplitude within the range in order to vary the stimulation therapy. In other examples, the variation between pulses may be limited according to a weighted randomization to a target magnitude and/or limited to the magnitude of change between consecutive pulses. For example, the weighted randomization may generate pulses with a large percentage of pulses having a voltage amplitude near the target magnitude. Alternatively, the difference in magnitude between subsequent pulses may be limited to a predetermined value or a percentage of the preceding pulse.

In addition to varying of voltage amplitude between pulses within each burst 78, bursts 78 of burst pattern 76 may contain pulses having different voltage amplitudes between subsequent bursts. In this manner, variation of voltage amplitude between pulses continues into subsequent bursts in order to produce bursts having continually changing pulses. In alternative embodiments, burst pattern 76 may only have variations in pulse voltage amplitude between pulses of the same burst. In other words, burst 78A has at least two pulses with different voltage amplitude and burst 78A is then repeated throughout burst pattern 76. Further, some other examples of burst pattern 76 may include at least two bursts having identical pulses.

FIG. 8B shows burst pattern 80 having multiple bursts 82A, 82B, 82C, 82D and 82E (collectively "bursts 82"). Burst pattern 80 is similar to burst pattern 76. However, bursts 82 of burst pattern 80 each may have pulses of the same voltage amplitude within each of the bursts. A anti-desensitization measure implemented in burst pattern 80 is that the voltage amplitude of the pulses only varies between subsequent bursts, not within any burst. As shown in FIG. 8B, the voltage amplitude of the pulses in burst 82A is smaller than the voltage amplitude of the pulses in burst 82B. In this manner, the tissue affected by the stimulation pulses may not become desensitized to bursts having the same voltage amplitude throughout therapy. The variation in pulses provided within burst pattern 80 may be governed by stimulator 12 in a similar manner as described in FIG. 8A. In other examples of burst pattern 80, two or more bursts may have pulses of the same voltage amplitude.

FIG. 8C shows multiple burst patterns 84A and 84B delivered to patient 16. Stimulator 12 may implement a desensitization measure that further varies the pulses of bursts throughout the treatment of the patient. In some examples, burst pattern 76 and 80 described above may be repeated whenever gastric stimulation is delivered to patient 16. In contrast, burst patterns 84A and 84B of FIG. 8C deliver bursts having pulses with different voltage amplitudes of the pulses. Burst pattern 84A contains at least burst 86A and 86B. The first burst 86A has pulses with smaller voltage amplitudes than pulses of burst 86B. Burst pattern 84B is different than burst pattern 84A such that first burst 88A has pulses with greater voltage amplitudes than the pulses of burst 88B. While burst patterns 84A and 84 may include two bursts or greater than one hundred bursts, stimulator 12 or programmer 14 may vary at least one burst between the two burst patterns in order to implement the desensitization measure.

While the bursts shown in FIGS. 8A, 8B and 8C, each have six pulses, bursts delivered to patient 16 may have any number of pulses as desired by the clinician to treat the patient. In addition, burst patterns 76, 80, 84A or 84B may have any number of bursts. The number of bursts within subsequent burst patterns may vary with the length of each burst pattern and/or the duty cycle of the pulses and bursts. In any case, stimulator 12 may vary at least one stimulation parameter within a burst, burst pattern, or treatment of patient 16 in order to implement a desensitization measure. This implementation is not directed to changing the efficacy of therapy. Rather, the variation of stimulation parameters is directed to extending the efficacy of therapy by preventing the constant delivery of identical stimulation therapy to a tissue site or sites.

Figure 9:
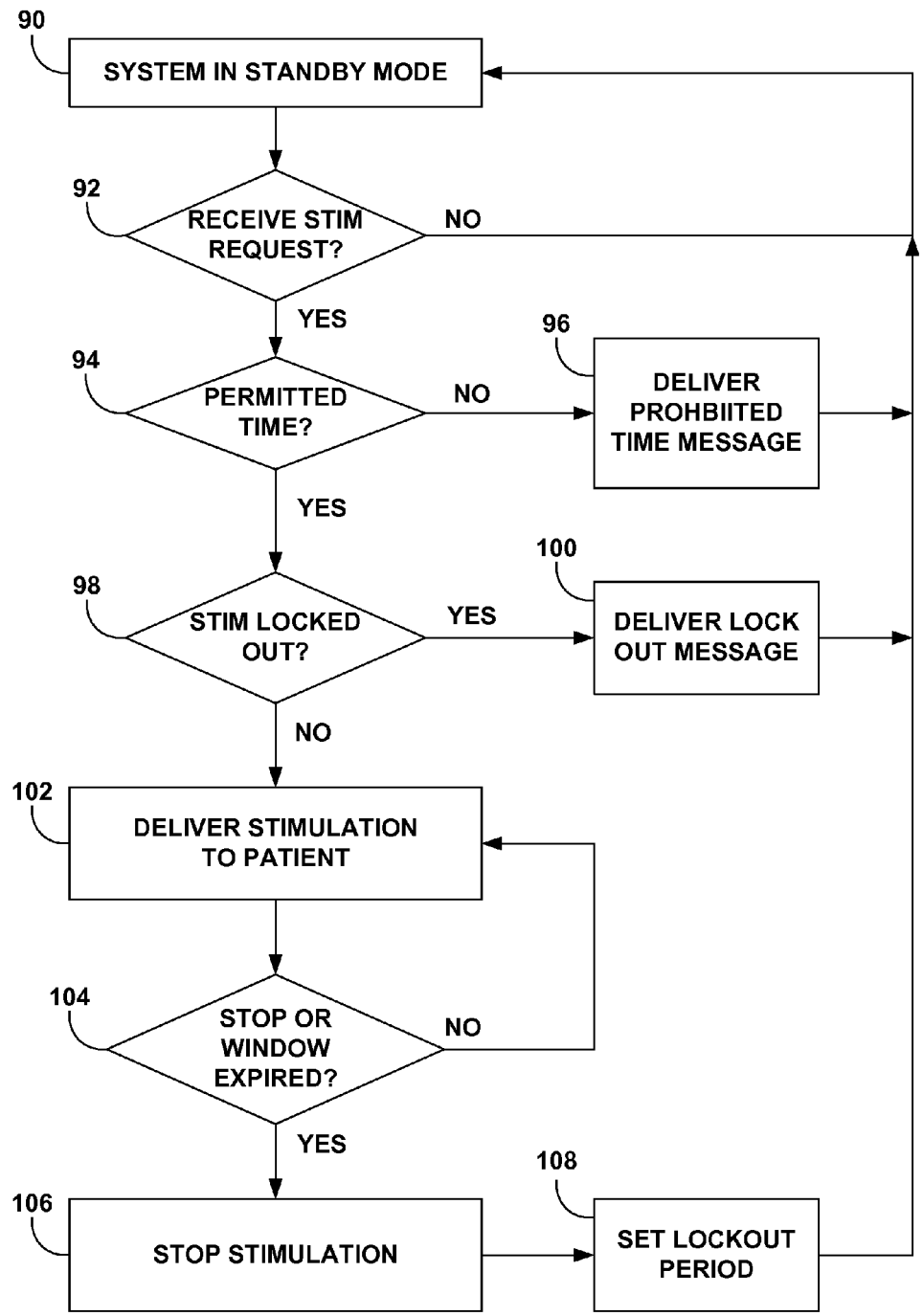
FIG. 9 is a flow diagram illustrating a method for delivering gastric stimulation therapy according to a lockout period that extends the efficacy of the therapy.

FIG. 9 is a flow diagram illustrating a method for delivering gastric stimulation therapy according to a lockout period that extends the efficacy of the therapy. It will be apparent that the method illustrated in FIG. 9 may be implemented within a patient programmer, a gastric electrical stimulator, or a combination of both. In general, one of the programmer or the stimulator receives a request to deliver the electrical gastric stimulation therapy to the patient, prohibits delivery of the gastric stimulation therapy by the stimulator if the request is received within a lockout period following a previous delivery of gastric stimulation therapy, and permits delivery of the gastric stimulation therapy by the stimulator if the request is not received within a lockout period following the previous delivery of gastric stimulation therapy.

As shown in FIG. 9, system 10 stands ready in standby mode where the system is ready to deliver therapy when needed (90). If system 10 does not receive a request or indication for stimulation therapy (92), the system remains in standby mode. If system 10 receives a request to deliver stimulation (92), e.g., by user input into patient programmer 14, a command received by stimulator 12 from patient programmer 14, or a command generated automatically within stimulator 12 or programmer 14, e.g., for delivery of stimulation at a scheduled time, system 10 checks to determine if the stimulation request is made at a permitted time on a therapy schedule (94).

If not, then patient programmer 14 may deliver a prohibited time message to patient 16 (96), advising the patient that stimulation is not permitted. In this manner, patient programmer 14 or stimulator 12 prohibit delivery of gastric stimulation therapy if a request is not received within a time period specified by the therapy schedule. The system 10 then may return to standby mode (90). If the stimulation request is made at a permitted time (94), then patient programmer 14 may determine if stimulation is nevertheless locked out via a lockout period (98) following a termination of a previous application of therapy. If system 10 is locked out from delivering therapy, system 10 delivers a lockout message to patient 16, e.g., via patient programmer 14, that indicates therapy cannot be delivered at this time (100). System 10 then may return to standby mode (90).

If system 10 is not locked out, the system delivers electrical stimulation to patient 16 via stimulator 12 (102). If a stop request is received (104), e.g., from patient 16 via patient programmer 14, the patient programmer instructs stimulator 12 to stop stimulation (106). Similarly, if a stop request has not been received but an applicable therapy window has expired (104), patient programmer 14 instructs stimulator 12 to stop stimulation (106). In this manner, stimulator 12 may receive an instruction from programmer 14 to generate the stimulation for the first period of time corresponding to the therapy window. Alternatively, stimulator 12 may voluntarily stop stimulation if the stimulator is configured to track the therapy window. If no stop request is received, and the therapy window has not expired, stimulator 12 continues to deliver therapy (102). Again, the therapy window may be selected to be a length of time sufficient to cause a desired therapeutic effect for a desired period of time, taking into account any prolonged therapeutic effect that may during a recovery period following cessation of the stimulation therapy.

When stimulation is complete and stimulator 12 stops delivering electrical stimulation to patient 16 (106), system 10 sets the lockout period according to the lockout instructions stored by system 10 (108), e.g., in patient programmer 14 or stimulator 12. System 10 then any return to standby mode until stimulation therapy is to be delivered again (90). In some embodiments, system 10 may also implement additional anti-desensitization features to further extend the efficacy of gastric stimulation therapy. For example, in addition to the lockout, therapy schedule and therapy window features, programmer 14 and/or stimulator 12 may deliver stimulation using burst pattern parameter selection, a burst pattern variation feature, or multi-site features.

Figure 10:
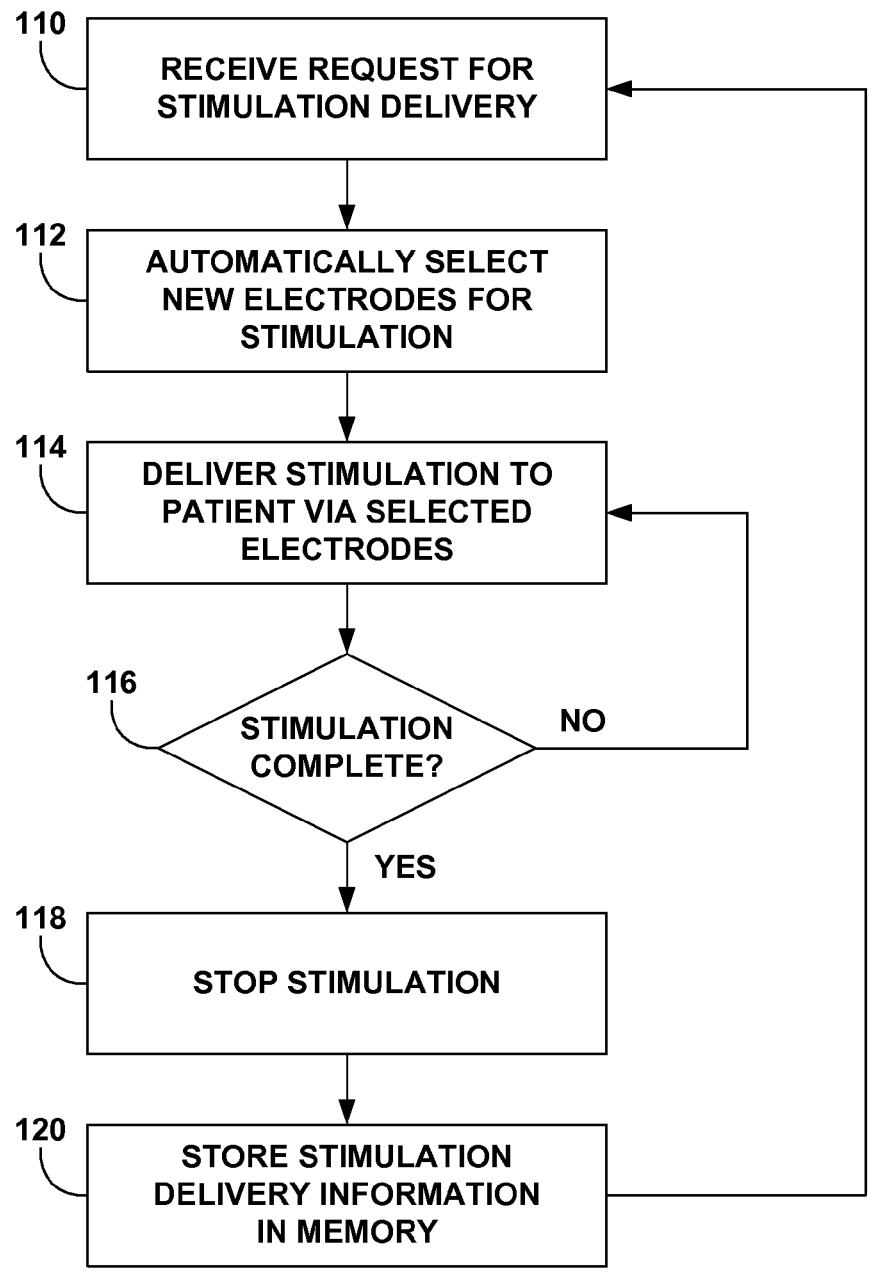
FIG. 10 is a flow diagram illustrating a method for delivering gastric electrical stimulation therapy according to a combination of electrodes selected to extend the efficacy of the therapy.

FIG. 10 is a flow diagram illustrating a method for delivering gastric stimulation therapy according to a selection of electrode combinations to extend the efficacy of the therapy. It will be apparent that the method illustrated in FIG. 10 may be implemented within a patient programmer, a gastric electrical stimulator, or a combination of both. As shown in FIG. 10, system 10 remains in standby mode until a request for stimulation delivery is received (110). The request may be a patient input that requests stimulation therapy, which may be entered into patient programmer 14. Alternatively, the request may be a command transmitted by patient programmer 14 to stimulator 12. As a further alternative, the request may be a command generated automatically within patient programmer 14 or stimulator 12. In this example, system 10 generates a selection of electrodes, either in patient programmer 14 or stimulator 12, by automatically selecting new, available electrodes for electrical stimulation (112) according to a predetermined order, a random selection function, or a pseudo-random selection function. The electrodes may be selected from one or more arrays of multiple electrodes, e.g., as shown in FIG. 4, to form different electrode combinations for use in multi-site stimulation.

Random or pseudo-random selection may be used within programmer 14 and/or stimulator 12 to produce a selected combination of electrodes for delivery of stimulation. Alternatively, instead of random or pseudo-random selection, system 10 may select the electrodes according to a predetermined progression or scheme, which may be defined by a clinician. In either case, the selection is automatic by programmer 14 or stimulator 12. The electrode selection may be made by patient programmer 14, in which case the patient programmer transmits the selection to stimulator 12 for use in delivery of stimulation. Alternatively, stimulator 12 may voluntarily select the electrodes when patient programmer 14 instructs the stimulator to start stimulation. In each case, the electrode selection may be subject to constraints such that electrodes selected at different tissue sites are still sufficient to achieve a desired therapeutic effect.

The new electrodes associated with a newly selected electrode combination should be different from the electrodes in the electrode combination used for the last stimulation application, and should target a different stimulation site. The last stimulation may refer to stimulation delivered in a previous scheduled period S on the therapy schedule, during a previous therapy window W, during a previous time segment within a therapy window, or otherwise. For example, the electrode combination selection may be changed from one therapy window to another such that successive applications of stimulation therapy use different electrode combinations. Alternatively, the electrode selection may be changed from one scheduled time period to another, e.g., such that a patient receives stimulation via different electrodes at breakfast, lunch, dinner or other time periods.

The process of FIG. 10 also may be applicable to techniques that do no make use of therapy schedules, therapy windows, or the like. As an alternative, different sets of electrodes may be selected as electrode combinations for successive applications of stimulation, without regard to the manner in which the timing of the stimulation is determined. In each case, use of the same electrodes as electrode combinations is avoided for consecutive stimulation applications. In addition, the electrode selection may be changed for one pulse burst to another or for one burst pattern to another within the same therapy window or scheduled time period. As a further alternative, electrode selection may be changed at periodic intervals during the course of delivery of stimulation, e.g., every n seconds or minutes. Each electrode combination may be used to deliver stimulation for a period of time of greater than or equal to thirty seconds.

Stimulator 12 delivers electrical stimulation to patient 16 via the new selection of electrodes (114), either automatically or as instructed by patient programmer 14. Once electrical stimulation is complete (116), e.g., as a result of a patient request to stop stimulation or expiration of a therapy window, scheduled time period (FIG. 9), or other applicable time limit (such as a specified period of time for use of the electrode combination), stimulator 12 stops stimulation to cease therapy (118). Patient programmer 14 then may store stimulation delivery information for use or review at a later time (120). Stimulation delivery information may include any data relevant to the therapy. For example, stimulation delivery information may include stimulation parameters such as voltage, current, pulse width, pulse frequency, burst rate, and selection of electrodes. In addition, stimulation delivery information may also include any patient input to patient programmer 14, such as additional requests for stimulation or changes in stimulation amplitude during therapy.

While random selection of electrode combinations may be useful, patient programmer 14 may select electrode combinations based upon any of a variety of methods desired by the clinician. For example, patient programmer 14 may select electrodes by cycling through available electrodes, selecting electrodes according to an algorithm designed to limit desensitization of tissue, or some other method. As one example, a clinician or other caregiver may directly specify a fixed progression among successive, selected electrode combinations. In any case, patient programmer 14 or stimulator 12 changes the selection of electrode combinations to support multi-site stimulation as another anti-desensitization feature directed to extending the efficacy of the gastric stimulation therapy. The selection of different electrode combinations as an anti-desensitization feature, e.g., as illustrated in FIG. 10, may be practiced independently or in conjunction with other anti-desensitization features, e.g., lockout, therapy window, therapy schedule, and burst pattern parameter selection.

Figure 11:
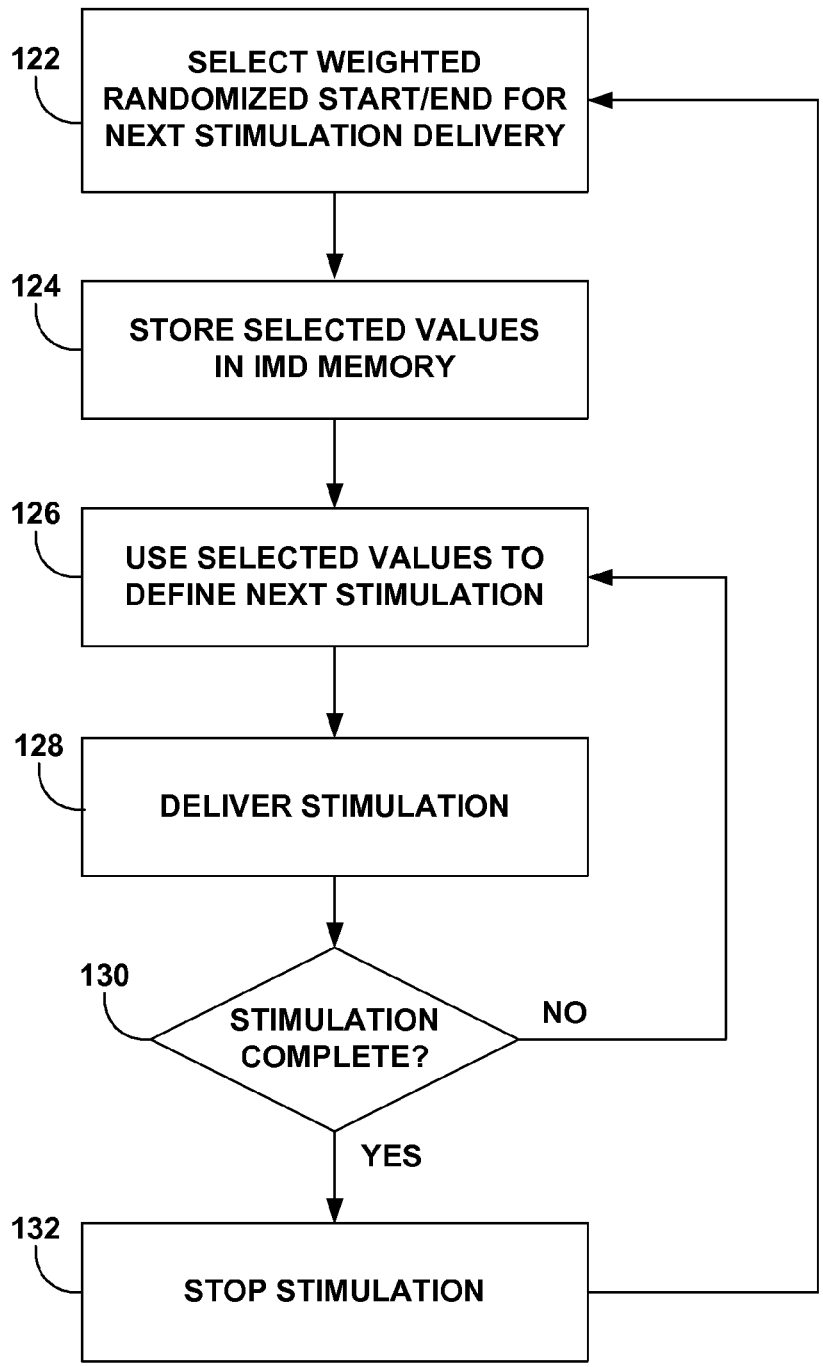
FIG. 11 is a flow diagram illustrating a method for delivering gastric electrical stimulation therapy at randomized start times to extend the efficacy of the therapy.

FIG. 11 is a flow diagram illustrating a method for delivering gastric stimulation therapy at with varying start times, end times, or durations. The method of FIG. 11 may be implemented within programmer 14 and/or stimulator 12 to adjust, e.g., timing and duration of burst patterns, or timing and duration of permitted time periods on a therapy schedule. As mentioned previously, start times and/or end times associated with permitted time periods on a therapy schedule may be adjusted. In this manner, the therapy schedule may ensure that stimulation is delivered not only at selected times, rather than continuously, but also at selected, variable times. Also, as mentioned previous, the number, timing and duration of burst patterns may be adjusted whether burst patterns are used in conjunction with a therapy schedule and therapy windows, or not.

In the example of FIG. 11, stimulator 12 or programmer 14 may select a weighted randomized start time for the next stimulation delivery (122), which may be coincident with the next permitted period of time on a therapy schedule, if applicable. Processors within stimulator 12 or programmer 14 may access instructions within memory to perform the start time selection process. The instructions may be in the form of a set of equations, for example, that weight the start times to a target start time so that the randomization of start times does not drift away from a preferred start time for therapy. For example, the instructions may be configured to generate a high percentage of start times within a predetermined number of minutes (e.g., 10 to 15 minutes) of the target start time. The clinician may alter the instructions at initial programming or throughout therapy.

The selected start time may vary relative to the start time for a previous stimulation delivery that was delivered, e.g., in a previous period P. In particular, the start time of a previous stimulation delivery in the same period P may not be relevant. Rather, the start time may be selected so that stimulation is not delivered at the same time during every period P, e.g., at the same time every day. For example, the start time of stimulation delivered around lunch time for a given day is varied relative to the start time of stimulation delivery around lunch time the previous day.

In addition to selecting a start time, stimulator 12 and/or programmer 14 may determine an end time using a similar technique, so that a duration of the stimulation delivery can be varied. Alternatively, the duration may be fixed while the start time is varied to change the timing of the stimulation delivery. Selecting different start time and end time may be useful for varying the timing and duration of burst patterns that are delivered with or without regard to a therapy schedule or therapy windows.

Variation of start time and/or end time ensures that the next stimulation delivery will not occur at the same time as the corresponding stimulation delivery in the previous period P. For example, if the corresponding start time was 9:05 AM the previous day, stimulator 12 or programmer 14 may be programmed select a start time so as to avoid a second day of starting therapy at 9:05 AM. Stimulator 12 or programmer 14 may store the selected start and/or end time value(s) in memory to determine the start of the next permitted period of time in the therapy schedule for delivery of therapy (124).

Stimulator 12 or programmer 14 then uses the selected values to define the next stimulation to be delivered (126). Therapy is then delivered when an internal clock or other timing device indicates that the time matches the selected start time in memory (128). If the stimulation delivery is not complete (130), e.g., no stop request, therapy window expiration, or therapy schedule time expiration applies, stimulator 12 continues stimulation delivery (128). Once stimulation is complete (130), stimulator 12 stops stimulation delivery to patient 16 (132) and selects the next start and/or end time value (122).

While stimulator 12 or programmer 14 are described in FIG. 11 as using a weighted randomized start time, stimulator 12 may vary the start time with any method desired by the clinician. For example, the start times may be cycled between multiple reselected start times, randomly selected within a given start time range, or selected based upon several previous start times to ensure start time variation. In any case, the variation of start times may prevent the stimulated tissue from becoming accustomed to stimulation at a certain static time during the day. In addition, variation of start times may prevent patient 16 from altering their eating habits to accommodate the stimulation therapy delivery times.

Figure 12:
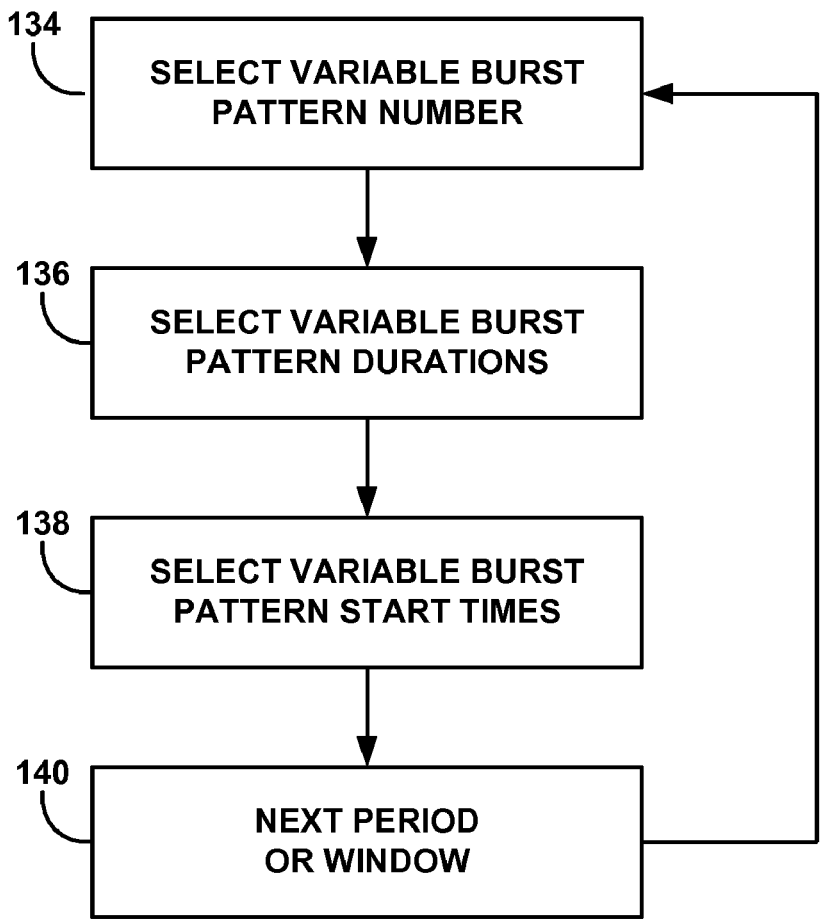
FIG. 12 is a flow diagram illustrating a method for selecting different burst pattern characteristics for gastric electrical stimulation to extend efficacy of therapy.

FIG. 12 is a flow diagram illustrating a method for selecting different burst pattern characteristics to extend efficacy of therapy. As shown in FIG. 12, programmer 14 and/or stimulator 12 may select a variable burst pattern number (134), variable burst pattern durations (136) and variable burst pattern start times (138) for each therapy period or window. In this manner, different numbers of burst patterns can be delivered in different therapy periods, e.g., different days. In addition, the burst patterns on different days may have different durations and start times. Likewise, if stimulator 12 is configured to delivered more than one burst pattern within a therapy window, the number, duration and start times of the burst patterns may be varied. In this manner, burst patterns can be modified to assist in preventing or delaying desensitization.

Figure 13:
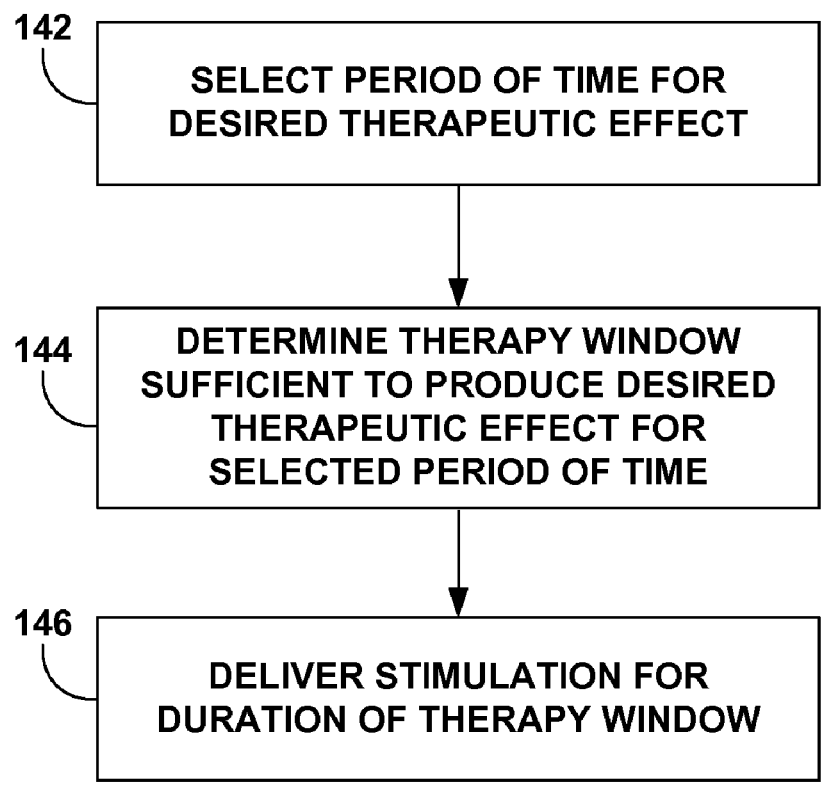
FIG. 13 is a flow diagram illustrating application of a therapy window feature for gastric electrical stimulation to extend efficacy of therapy.

FIG. 13 is a flow diagram illustrating application of a therapy window feature as described herein for gastric electrical stimulation to extend efficacy of therapy. In the example of FIG. 13, a period of time for a desired therapeutic effect is selected (142). For example, a physician or patient may select the time of the desired therapeutic effect to persist, e.g., via a programmer. A programmer or stimulator determines a therapy window that is sufficient to produce the desired therapeutic effect for the selected period of time (144), e.g., given a set of stimulation parameters. For example, the programmer or stimulator may refer to preestablished data mapping the selected period of time to one of a plurality of therapy windows, or apply a mathematical function that computes a therapy window for the selected period of time. The data or function may be formulated based on theoretical or empirical data obtained for the patient or for a class of patients. Again, different therapy windows, i.e., of different lengths, may be predetermined for different therapeutic effects and different periods of time for which the therapeutic effects are desired. Accordingly, when a desired therapeutic effect is desired for a particular period of time, the effect and the time can be mapped to an appropriate therapy window using the preestablished mapping. The stimulator then delivers the stimulation for the duration of the therapy window (146) to produce the desired therapeutic effect for the selected period of time, which extends beyond the end of the therapy window.

Figure 14:
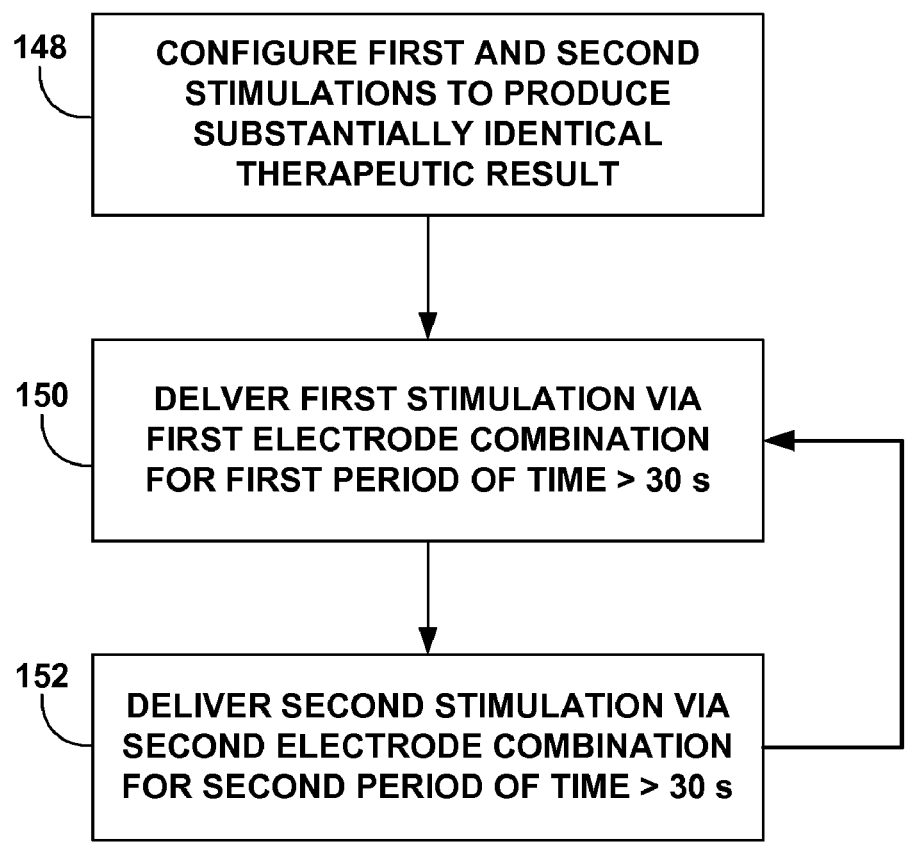
FIG. 14 is a flow diagram illustrating application of a multi-site stimulation feature for gastric electrical stimulation to extend efficacy of therapy.

FIG. 14 is a flow diagram illustrating application of a multi-site stimulation feature as described herein for gastric electrical stimulation to extend efficacy of therapy. In the example of FIG. 14, a programmer or stimulator configures first and second stimulation therapies to produce a substantially identical therapeutic result (148), such as distention. For example, parameters associated with the first and second stimulation may be programmed to produce the substantially identical therapeutic result. In some cases, the parameters used for the first and second stimulation may be substantially identical. The stimulator then may apply the first and second stimulation to different sites via different electrode combinations. As shown in FIG. 14, the stimulator may deliver the first stimulation via a first electrode combination for a first period of time greater than or equal to approximately thirty seconds (150), and delivered the second stimulation via a second electrode combination for a second period of time greater than or equal to approximately thirty seconds (152). The first and second periods of time may partially overlap or not overlap, and may be the same or different in duration.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure.

Various aspects of the disclosure have been described. These and other aspects are within the scope of the following claims.

The invention claimed is:

1. A method comprising delivering electrical stimulation therapy to a gastrointestinal organ of a patient for a first period of time, wherein the first period of time is selected to produce a desired therapeutic effect for a second period of time that extends at least in part beyond an end of the first period of time, and wherein the desired therapeutic effect includes a change in gastric muscle tone indicated by a degree of gastric distention.

2. The method of claim 1, wherein the second period of time is greater than the first period of time.

3. The method of claim 1, wherein the first period of time is selected as approximately a minimum period of time sufficient to produce the desired therapeutic effect for the second period of time.

4. The method of claim 1, wherein the degree of gastric distention corresponds to a percentage increase in gastric volume.

5. The method of claim 1, wherein delivering electrical stimulation therapy to a gastrointestinal organ of a patient for a first period of time comprises delivering electrical stimulation therapy to one of a stomach or a small intestine of the patient.

6. The method of claim 1, further comprising receiving an instruction from an external programmer to generate the electrical stimulation therapy for the first period of time.

7. A gastric electrical stimulation device comprising:
means for generating electrical stimulation therapy for a first period of time; and
means for delivering the electrical stimulation therapy to a gastrointestinal organ of a patient,
wherein the first period of time is selected to produce a desired therapeutic effect for a second period of time that extends at least in part beyond an end of the first period of time, and
wherein the desired therapeutic effect includes a change in gastric muscle tone indicated by a degree of gastric distention.

8. The device of claim 7, wherein the second period of time is greater than the first period of time.

9. The device of claim 7, wherein the first period of time is selected as approximately a minimum period of time sufficient to produce the desired therapeutic effect for the second period of time.

10. The device of claim 7, wherein the degree of gastric distention corresponds to a percentage increase in gastric volume.

11. The device of claim 7, wherein the gastrointestinal organ is one of a stomach or a small intestine of the patient, and the electrical stimulation is configured to produce the desired therapeutic effect in the stomach or the small intestine.

12. The device of claim 7, further comprising means for receiving an instruction from an external programmer to generate the electrical stimulation therapy for the first period of time.

13. A gastric electrical stimulation device comprising:
- an electrical stimulation generator that generates electrical stimulation therapy for a first period of time;
- one or more implantable electrodes coupled to deliver the electrical stimulation therapy to a gastrointestinal organ of a patient,
- wherein the first period of time is selected to produce a desired therapeutic effect for a second period of time that extends at least in part beyond an end of the first period of time, and
- wherein the desired therapeutic effect includes a change in gastric muscle tone indicated by a degree of gastric distention.

14. The device of claim 13, wherein the second period of time is greater than the first period of time.

15. The device of claim 13, wherein the first period of time is selected as approximately a minimum period of time sufficient to produce the desired therapeutic effect for the second period of time.

16. The device of claim 13, wherein the degree of gastric distention corresponds to a percentage increase in gastric volume.

17. The device of claim 13, wherein the gastrointestinal organ is one of a stomach or a small intestine of the patient, and the electrical stimulation is configured to produce the desired therapeutic effect in the stomach or the small intestine.

18. The device of claim 13, further comprising a telemetry interface that receives an instruction from an external programmer to generate the electrical stimulation therapy for the first period of time.

19. An external programmer device for a gastric electrical stimulator, the programmer comprising a processor that controls the electrical stimulator to generate electrical stimulation therapy for a first period of time for delivery to a gastrointestinal organ of a patient, wherein the first period of time is selected to produce a desired therapeutic effect for a second period of time that extends at least in part beyond an end of the first period of time, and wherein the desired therapeutic effect includes a change in gastric muscle tone indicated by a degree of gastric distention.

20. The device of claim 19, wherein the second period of time is greater than the first period of time.

21. The device of claim 19, wherein the first period of time is selected as approximately a minimum period of time sufficient to produce the desired therapeutic effect for the second period of time.

22. The device of claim 19, wherein the degree of gastric distention corresponds to a percentage increase in gastric volume.

23. The device of claim 19, wherein the gastrointestinal organ is one of a stomach or a small intestine of the patient, and the electrical stimulation is configured to produce the desired therapeutic effect in the stomach or the small intestine.

24. The device of claim 19, further comprising a telemetry interface that transmits the instruction to cause the electrical stimulation generator to generate the electrical stimulation therapy for the first period of time.

25. A method comprising:
- selecting a first period of time, for delivery of electrical stimulation therapy to a gastrointestinal organ of a patient, sufficient to produce a desired therapeutic effect for a second period of time that extends at least in part beyond an end of the first period of time; and
- controlling an electrical stimulator to deliver the electrical stimulation therapy to the gastrointestinal organ of the patient for the first period of time, wherein the desired therapeutic effect includes a change in gastric muscle tone indicated by a degree of gastric distention.

26. The method of claim 25, wherein the first period of time is selected as approximately a minimum period of time sufficient to produce the desired therapeutic effect for the second period of time.

* * * * *